US010085766B1

United States Patent
Mustapha

(10) Patent No.: US 10,085,766 B1
(45) Date of Patent: Oct. 2, 2018

(54) CHRONIC TOTAL OCCLUSION CROSSING DEVICES AND METHODS

(71) Applicant: Jihad A. Mustapha, Grandville, MI (US)

(72) Inventor: Jihad A. Mustapha, Grandville, MI (US)

( * ) Notice: Subject to any disclaimer, the term of this patent is extended or adjusted under 35 U.S.C. 154(b) by 0 days.

(21) Appl. No.: 15/666,279

(22) Filed: Aug. 1, 2017

Related U.S. Application Data

(60) Provisional application No. 62/479,646, filed on Mar. 31, 2017, provisional application No. 62/500,303, filed on May 2, 2017.

(51) Int. Cl.

| | | |
|---|---|---|
| *A61B 17/22* | (2006.01) | |
| *A61D 1/02* | (2006.01) | |
| *A61B 17/3207* | (2006.01) | |
| *A61M 25/00* | (2006.01) | |

(Continued)

(52) U.S. Cl.
CPC ...... *A61B 17/320783* (2013.01); *A61B 17/22* (2013.01); *A61M 25/0026* (2013.01); *A61B 2017/00867* (2013.01); *A61B 2017/22042* (2013.01); *A61B 2017/22094* (2013.01);

(Continued)

(58) Field of Classification Search
CPC .... A61B 17/320725; A61B 17/320758; A61B 17/221; A61B 17/22; A61B 17/22031; A61B 17/12109; A61B 17/32037; A61B 17/1214; A61B 2017/2212; A61B 2017/22094; A61B 2017/320733; A61B 2017/22034; A61B 2017/320004; A61B 2017/22038; A61B 2017/22031; A61B 2017/00867; A61B 2017/22042; A61B 2017/22044; A61B 2017/22067; A61B 2017/22068; A61B 2017/22069; A61B 2017/320064; A61B 2017/320052; A61B 2017/00358; A61B 2017/22077; A61B 2017/320056; A61M 25/104;

(Continued)

(56) References Cited

U.S. PATENT DOCUMENTS

| | | | |
|---|---|---|---|
| 4,943,289 A | 7/1990 | Goode et al. | |
| 5,387,219 A | 2/1995 | Rappe | |
| 5,551,443 A | 9/1996 | Sepetka et al. | |

(Continued)

FOREIGN PATENT DOCUMENTS

| | | |
|---|---|---|
| DE | 102007042531 A1 | 3/2009 |
| WO | 2016001712 A2 | 1/2016 |
| WO | 2016133932 A1 | 8/2016 |

OTHER PUBLICATIONS

James B. Park et al., Supplement to Endovascular Today, Master the Cross, Mar. 2014, pp. 1-24.

(Continued)

*Primary Examiner* — Elizabeth Houston
*Assistant Examiner* — Mohamed Gabr
(74) *Attorney, Agent, or Firm* — Venable LLP; Michele V. Frank

(57) ABSTRACT

A device for crossing a lesion in a tissue lumen includes a crossing wire configured to pass through a lumen of a catheter, the crossing wire including a loop at a distal end of the crossing wire, the loop having a configuration that prevents a width of the loop from exceeding a width of the tissue lumen, and the loop having a leading portion configured to interrogate the lesion.

21 Claims, 21 Drawing Sheets

(51) Int. Cl.
    *A61B 17/00*     (2006.01)
    *A61B 90/00*     (2016.01)

(52) U.S. Cl.
    CPC ............ *A61B 2017/320791* (2013.01); *A61B 2090/3966* (2016.02); *A61M 2025/0004* (2013.01)

(58) Field of Classification Search
    CPC .............. A61M 25/0074; A61M 25/09; A61M 25/0043; A61M 2025/09183
    See application file for complete search history.

(56) References Cited

U.S. PATENT DOCUMENTS

| | | | |
|---|---|---|---|
| 5,772,609 A | 6/1998 | Nguyen et al. | |
| 5,989,266 A | 11/1999 | Foster | |
| 6,146,397 A | 11/2000 | Harkrider, Jr. | |
| 6,165,200 A * | 12/2000 | Tsugita | A61F 2/01 606/200 |
| 6,299,612 B1 | 10/2001 | Ouchi | |
| 6,620,179 B2 | 9/2003 | Boock et al. | |
| 7,041,116 B2 | 5/2006 | Goto et al. | |
| 7,520,881 B2 | 4/2009 | Foushee et al. | |
| 7,621,880 B2 | 11/2009 | Ryan et al. | |
| 7,753,919 B2 | 7/2010 | Kanamaru | |
| 9,113,955 B2 | 8/2015 | Noriega et al. | |
| 9,295,813 B2 | 3/2016 | Kanazawa et al. | |
| 9,693,795 B2 | 7/2017 | Avneri et al. | |
| 9,717,513 B2 | 8/2017 | Golan | |
| 2004/0215109 A1 | 10/2004 | Pingleton et al. | |
| 2005/0234474 A1 | 10/2005 | DeMello et al. | |
| 2007/0213584 A1 | 9/2007 | Kim et al. | |
| 2008/0033423 A1 | 2/2008 | Peacock | |
| 2008/0064988 A1 * | 3/2008 | Carter | A61M 25/09 600/585 |
| 2008/0194993 A1 * | 8/2008 | McLaren | A61M 25/09 600/585 |
| 2009/0182363 A1 | 7/2009 | Shamay | |
| 2009/0264907 A1 | 10/2009 | Vrba et al. | |
| 2010/0100055 A1 | 4/2010 | Mustapha | |
| 2011/0034937 A1 | 2/2011 | Mustapha et al. | |
| 2015/0151081 A1 | 6/2015 | Keith et al. | |
| 2016/0038164 A1 | 2/2016 | Katoh et al. | |
| 2016/0096000 A1 | 4/2016 | Mustapha | |
| 2016/0135881 A1 | 5/2016 | Katoh et al. | |
| 2016/0183963 A1 | 6/2016 | Richter et al. | |
| 2016/0235948 A1 | 8/2016 | Sina | |
| 2017/0209162 A1 | 7/2017 | Sperry et al. | |

OTHER PUBLICATIONS

Qian et al., "Guidewire Looping Technique for Re-Canalizing Chronic Long-Segment Occlusions of Femoropopliteal Arteries", Journal of Interventional Radiology, vol. 18(12), 2009, pp. 893-895 (w/ English abstract).

Wang et al., "An Effective Guidewire Looping Technique for the Recanalization of Occlusive Segments of Infrapopliteal Vessels", Korean Journal of Radiology, vol. 11(4), Jul./Aug. 2010, pp. 441-448.

"Fisherbrand Twisted Nichrome Inoculating Loops with Handles": Diagnostic; Available in three loop sizes; Fisher Scientific; https://www.fishersci.com/shop/products/fisherbrand-twisted-nichrome-inoculating-loops-handles-6/p-180513.

* cited by examiner

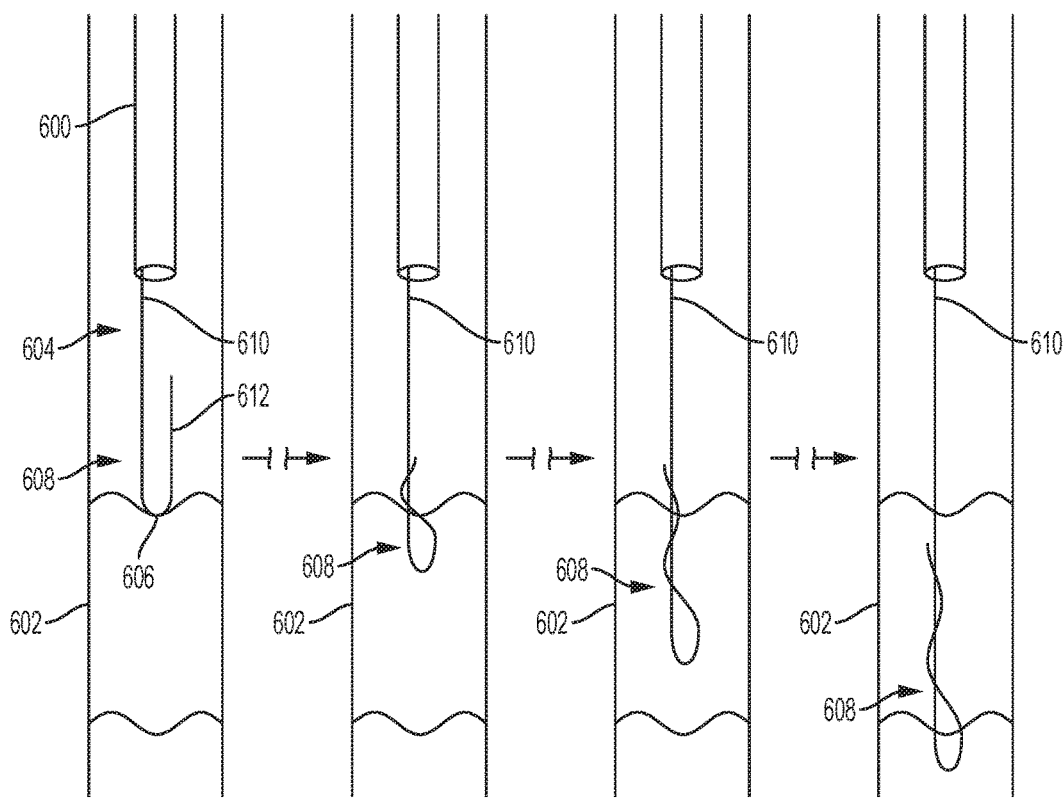

CHRONIC TOTAL OCCLUSION CROSSING DEVICES AND METHODS

This application claims priority to U.S. Provisional Application No. 62/479,646 filed Mar. 31, 2017 and U.S. Provisional Application No. 62/500,303 filed May 2, 2017, the entire contents of both of which are hereby incorporated by reference.

BACKGROUND

1. Technical Field

The field generally relates to crossing lesions in the vasculature, especially those referred to as a chronic total occlusions (CTO), and, more particularly crossing devices and methods utilizing a loop feature.

2. Discussion of Related Art

Vascular occlusions and, especially, CTOs can have a severe impact on a patient's health and lifestyle. CTOs are frequently encountered during endovascular interventions. CTOs exist in many patients with symptomatic peripheral arterial disease. In the lower extremities, CTOs are commonly encountered in the superficial femoral artery (SFA). Crossing these lesions may be challenging and may lead to prolonged procedure time, increased operator and patient radiation exposure, high contrast load, and peri-procedural complications including perforation, dissection, loss of collaterals, and creation of an arteriovenous fistula.

Revascularization of CTOs is usually hindered by failure to cross the lesion due to a variety of factors, so attempts to revascularize heavily calcified CTOs still can meet with failure. Existing CTO crossing devices still have a higher failure rate than desirable. Further, existing devices are too large to use in the vasculature below the waist. There remains an unmet need for devices and methods that can reliably and effectively cross lesions.

There further remains a need for devices and methods that can be used below the waist, including in the legs, such as the legs of diabetic patients that experience particularly difficult blockages, including peripheral artery disease (PAD). Such devices and methods would allow physicians to reliably and effectively cross the CTO without consequences such as perforating the vessel wall while attempting to cross the CTO. There remains an unmet need for effective and reliable treatment options for crossing CTOs.

SUMMARY

A device for crossing a lesion in a tissue lumen includes a crossing wire configured to pass through a lumen of a catheter, the crossing wire including a loop at a distal end of the crossing wire, the loop having a configuration that prevents a width of the loop from exceeding a width of the tissue lumen, and the loop having a leading portion configured to interrogate the lesion.

According to one aspect, the device further includes the catheter, wherein the catheter has a proximal end and a distal end. According to one aspect, a first proximal side of the loop is configured to be disposed within the lumen of the catheter, and a second proximal side of the loop is configured to be disposed outside of the lumen of the catheter. According to one aspect, a first proximal side of the loop and a second proximal side of the loop are configured to be disposed within the lumen of the catheter.

According to one aspect, the catheter further includes a hole in a side surface of the catheter, wherein a first proximal side of the loop is configured to be disposed within the lumen of the catheter, and wherein a second proximal side of the loop is configured to enter the lumen of the catheter through the hole in the side surface of the catheter.

According to one aspect, the crossing wire is twistable to form a loop having opposite sides that are intertwined. According to one aspect, the loop has a relaxed state such that opposite sides of the loop form an angle that is less than 90 degrees. According to one aspect, the loop has a relaxed state such that opposite sides of the loop form an angle that is less than 60 degrees.

According to one aspect, the leading portion of the loop is rounded. According to one aspect, the leading portion of the loop is flat. According to one aspect, the leading portion of the loop is pointed.

According to one aspect, the crossing wire is integrally formed. According to one aspect, the crossing wire has a single stiffness along its length. According to one aspect, the crossing wire has a variable stiffness along its length. According to one aspect, the crossing wire has a cross-section that is rectangular.

According to one aspect, the device further includes a stationary inner catheter disposed within the catheter, the stationary inner catheter including a second lumen therein. An outer surface of the stationary inner catheter is fixed to an inner surface of the catheter. According to one aspect, the device further includes a mobile inner catheter disposed within the lumen of the catheter eccentric to the stationary inner catheter, the mobile inner catheter forming a third lumen therein, the mobile inner catheter configured to move axially and radially with respect to the stationary inner catheter. According to one aspect, a first proximal side of the loop is configured to be disposed within the second lumen, and a second proximal side of the loop is configured to be disposed within the third lumen.

According to one aspect, the crossing wire is an elongated wire. The crossing wire has a proximal end controllable by a user, wherein the distal end of the crossing wire is configured for positioning in the tissue lumen for crossing a chronic total occlusion, the distal end including the loop, the loop having a pair of lateral opposing portions configured for alignment with a wall of the tissue lumen and the leading portion interconnecting the pair of lateral opposing portions, wherein the loop is configured for crossing the chronic total occlusion.

According to one aspect, the proximal end of the crossing wire has a first stiffness, and wherein the leading portion of the loop has a second stiffness, wherein the first stiffness is greater than the second stiffness. According to one aspect, the loop includes a material that is radiopaque. According to one aspect, the proximal end of the crossing wire forms a portion of a primary shaft of the crossing wire, wherein one of the pair of lateral opposing portions of the loop is directly connected to the primary shaft, and wherein another of the pair of lateral opposing portions is directly connected to a secondary shaft of the crossing wire, the secondary shaft being configured to wrap around the primary shaft.

According to one aspect, the crossing wire is configured to be rotatable back and forth through an angle less than 360 degrees while maintaining contact with the lesion to erode the lesion. According to one aspect, the crossing wire is configured to be twisted through an angle greater than 360 such that lateral opposing portions of the crossing wire become entwined beyond the distal end of the catheter.

A method for crossing a chronic total occlusion (CTO) includes inserting a catheter having a looped wire disposed in a lumen of the catheter into an occluded vessel; extending a distal end of the looped wire beyond a distal end of the catheter to contact an occlusion; grasping the looped wire at a position proximal to a proximal end of the catheter; and rotating the grasped looped wire back and forth through an angle less than 360 degrees while maintaining the distal end of the looped wire in contact with the occlusion to erode the occlusion.

According to one aspect, the method further includes twisting the grasped looped wire through an angle greater than 360 degrees while pressing the distal end of the looped wire against the occlusion such that sides of the looped wire become entwined beyond the distal end of the catheter.

A device for crossing a lesion in a tissue lumen includes a catheter forming a lumen; and a crossing wire configured to pass through the lumen of the catheter, the crossing wire including a primary shaft and a loop at a distal end of the primary shaft, the loop having a configuration that prevents a width of the loop from exceeding a width of the tissue lumen, and the loop having a leading portion configured to interrogate the lesion. The crossing wire has a first configuration in which opposing lateral sides of the loop are not twisted or are twisted by a first amount, and a second configuration wherein the opposing lateral sides of the loop are twisted by a second amount that is different from the first amount. The crossing wire can be changed from the first configuration to the second configuration by twisting the primary shaft at a position proximal to the catheter.

According to one aspect, a first side of the opposing lateral sides of the loop is directly connected to the primary shaft, a second side of the opposing lateral sides of the loop is directly connected to a secondary shaft of the crossing wire, and the primary shaft and the secondary shaft are disposed inside the lumen of the catheter. According to one aspect, in the second configuration, the opposing lateral sides of the crossing wire twist about each other a plurality of times. According to one aspect, a shape of the loop at a position distal to the catheter is configured to change when a rotational force is applied to the primary shaft at a position proximal to the catheter.

A device for crossing a lesion includes a catheter including a lumen, the catheter having a proximal end and a distal end, and a crossing wire configured to pass through lumen, the crossing wire including a loop at a distal end of the crossing wire, the loop having a relaxed state such that opposite sides of the loop form an angle that is less than 180 degrees, and the loop having a leading portion configured to interrogate the lesion.

According to one aspect, a first proximal side of the loop is configured to be disposed within lumen of the catheter, and a second proximal side of the loop is configured to be disposed outside of the lumen of the catheter. According to one aspect, a first proximal side of the loop and a second proximal side of the loop are configured to be disposed within lumen of the catheter. According to one aspect, the catheter further includes a hole in a side surface of the catheter, wherein a first proximal side of the loop is configured to be disposed within the lumen of the catheter, and wherein a second proximal side of the loop is configured to enter the lumen of the catheter through the hole in the side surface of the catheter.

According to one aspect, the crossing wire is twistable to form a loop having opposite sides that are intertwined. According to one aspect, the loop has a relaxed state such that opposite sides of the loop form an angle that is less than 90 degrees. According to one aspect, a first proximal side and a second proximal side of the loop are configured to be disposed within lumen of the catheter. According to one aspect, the loop has a relaxed state such that opposite sides of the loop form an angle that is less than 60 degrees. According to one aspect, the leading portion of the loop is rounded. According to one aspect, the leading portion of the loop is flat. According to one aspect, the leading portion of the loop is pointed.

According to one aspect, the crossing wire is integrally formed. According to one aspect, the crossing wire has a single stiffness along its length. According to one aspect, the crossing wire has a variable stiffness along its length. According to one aspect, the wire has a cross-section that is rectangular.

According to one aspect, the device further includes a stationary inner catheter disposed within the support catheter, the stationary inner catheter including a second lumen therein. An outer surface of the stationary inner catheter is fixed to an inner surface of the support catheter.

According to one aspect, the device further includes a mobile inner catheter disposed within the lumen of the support catheter eccentric to the stationary inner catheter, the mobile inner catheter forming a third lumen therein, the mobile inner catheter configured to move axially and radially with respect to the stationary inner catheter.

According to one aspect, a first proximal side of the loop is configured to be disposed within the second lumen, and a second proximal side of the loop is configured to be disposed within the third lumen.

A device for crossing a lesion includes a catheter including a lumen, the catheter having a proximal end and a distal end, and a crossing wire configured to pass through lumen, the crossing wire including a loop at a distal end of the crossing wire, the loop having opposite sides that are disposed within the lumen, and the loop having a leading portion configured to interrogate the lesion.

A chronic total occlusion crossing wire includes an elongated wire configured to pass through a catheter lumen, the elongated wire having a proximal end controllable by a user and a distal end configured for positioning in a vessel for crossing the chronic total occlusion, the distal end including a loop having a pair of lateral opposing portions configured for alignment with a wall of the vessel and a leading portion interconnecting the pair of lateral opposing portions, wherein the loop is configured for crossing the chronic total occlusion.

According to one aspect, the proximal end of the elongated wire has a first stiffness, and the leading portion of the loop has a second stiffness, wherein the first stiffness is greater than the second stiffness. According to one aspect, the loop includes a material that is radiopaque. According to one aspect, the proximal end of the elongated wire forms a portion of a primary shaft of the elongated wire, wherein one of the lateral opposing portions of the loop is directly connected to the primary shaft, and wherein another of the lateral opposing portions is directly connected to secondary shaft of the elongated wire, the secondary shaft being configured to wrap around the primary shaft.

A method for crossing a chronic total occlusion (CTO) includes inserting a catheter having a looped wire disposed in a lumen of the catheter into an occluded vessel, and extending a distal end of the looped wire beyond a distal end of the catheter to contact an occlusion. The method further includes grasping the looped wire at a position proximal to a proximal end of the catheter, and rotating the grasped looped wire back and forth through an angle less than 360 degrees while maintaining the distal end of the looped wire in contact with the occlusion to erode the occlusion.

In one aspect, the method further includes twisting the grasped looped wire through an angle greater than 360 degrees while pressing the distal end of the wire against the occlusion such that sides of the looped wire become entwined beyond the distal end of the catheter.

BRIEF DESCRIPTION OF THE DRAWINGS

Further objectives and advantages will become apparent from a consideration of the description, drawings, and examples.

FIG. 6A shows a device in one aspect of the invention positioned in the vasculature with a CTO, and the crossing wire is shown extended from the catheter proximate the CTO cap.

FIG. 6B shows the device in FIG. 6A penetrating the CTO.

FIG. 6C shows the device of FIGS. 6A and 6B penetrating further into the CTO.

FIG. 6D shows the device of FIGS. 6A, 6B and 6C penetrating further into the CTO and crossing the CTO.

DETAILED DESCRIPTION

Figure 1A:
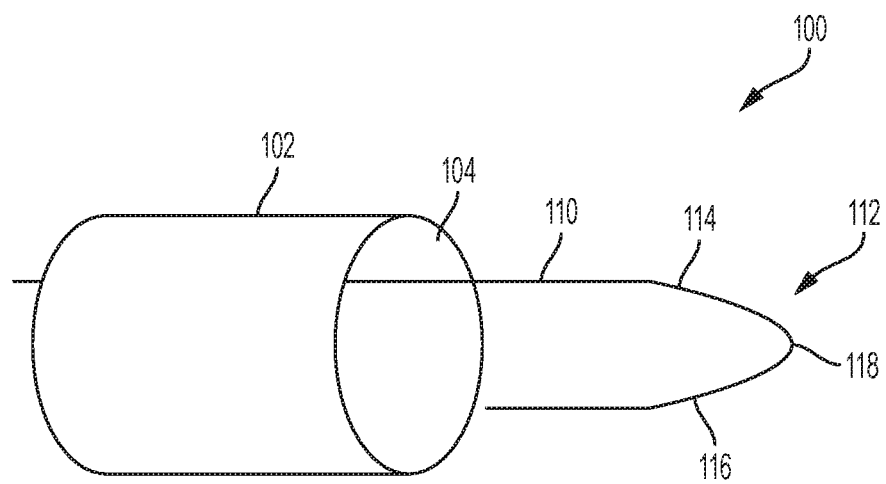
FIG. 1A shows a portion of a device for crossing a lesion according to one aspect of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The devices and methods contemplated are configured to reliably and effectively cross lesions in the vasculature, especially, lesions of the type where the accumulation of plaque is so severe that it results in a complete or nearly complete blockage of the vessel. The devices and methods in accordance with the principles of the invention are configured and adapted to cross an occlusion in order that interventional treatments can follow. The devices and methods described can include a crossing wire, a crossing catheter, and/or a combination of both utilized separately and/or in combination with each other and/or in combination with conventional wires and/or catheters.

The CTO crossing devices and methods can include a guidewire having a distal end configured for more reliably crossing a CTO. In one aspect this configured distal end can be referred to as a loop, as discussed in more detail below. This loop-ended crossing wire is configured to present a more reliable device for interaction and engagement with the CTO, and, more particularly, a cap of the CTO that can have varying geometries and complexities. The loop-ended crossing wire is also configured to present a more reliable device for advancing through the occlusion to successfully cross the lesion.

The configuration at the end of the guide wire, referred to as a loop, can include various geometries, shapes, sizes and material properties and can be configured by way of the contemplated methods alone and/or in combination with guidewires and/or catheters. The loop feature, and the associated methods and/or devices, can be configured to present an interrogation conducive distal leading end that balances loop resiliency with stiffness so as to present itself optimally to the lesion yet also allow the loop to pass through the lesion. The loop configuration can be achieved by shape-memory and/or arrangements of the wire alone, in combination with a catheter, and/or in combination with methods of use. For example, the guidewire loop can include a loop shape prior to use and/or a loop configuration that is formed in whole or in part in-situ, alone and/or in combination with a catheter.

A CTO crossing device according to some embodiments of the invention is directed to the concept of a loop at the distal end of the system, in particular, a guidewire loop. With this loop, the physician has the ability to use the leading distal end of the loop to interrogate the lesion and ultimately cross the lesion. The term "interrogate" as used herein can mean to contact, prod, probe, chip away at, break apart, dissect, and/or drill into a lesion. While interrogating a lesion may lead to crossing the lesion, the term "interrogating" is generally used to mean physically interacting with the lesion. The loop at the distal end of the system provides a stiffer surface for interrogating the lesion compared to, for example, using the floppy distal wire tip of a conventional guidewire.

Various aspects of the loop configuration can be considered. One aspect of the configuration is a dimensional configuration, such as the width of the loop. The width of the loop can be generally considered a lateral dimension. The width dimension of the loop can be configured based on the width or transverse dimension of the vessel in which the lesion is located. For example, the width may be configured to be half of the cross-sectional diameter of the vessel.

The loop can be configured to maintain geometries and/or configurations in use that allow crossing of the lesion without the loop collapsing and/or puncturing unintended areas of the vasculature. If the width of the loop exceeds the width of the vessel, or if the loop collapses, the vessel can rupture. The loop width can be selected to allow the loop to move along the vessel wall gently, without exerting point-like pressure on the vessel wall, and/or without exerting forces perpendicular to the vessel wall. According to one aspect, the width of the loop is between about 0.05 mm and about 6 mm. According to one aspect, the width of the loop is between about 1.5 mm and about 2.5 mm. According to one aspect, the width of the loop is between about 2.5 mm and about 6 mm.

In one aspect, the device can be configured to limit the width of the loop to be about half the width of the vessel. For example, for a 5 or 6 mm vessel, the width of the loop will less than about 2.5 or 3 mm. A narrow loop can move along the vessel wall without exerting point-like pressure on the vessel wall, and without exerting forces perpendicular to the vessel wall. If the width of the loop were allowed to expand such that it significantly exceeded the diameter of the vessel, the sides of the loop may exert forces perpendicular to the surface of the vessel wall that could puncture the vessel wall.

The loop can have a configuration that prevents a width of the loop from exceeding a width of the tissue lumen. The configuration may prevent the width of the loop from exceeding the width of the tissue lumen to the point of rupture, risk of rupture, undesirable stress and/or strain on the vessel, or beyond the vessel's elastic limits. In one aspect, the loop configuration may prevent the width of the loop from exceeding a width that is slightly greater than the diameter of the tissue lumen when no forces are being applied, because the shape of the lumen may change when an expanding force is applied by the loop, increasing the width of the lumen. In one aspect, the configuration may prevent the width of the loop from exceeding the width of the tissue lumen to the point of injury. In one aspect, the configuration may provide a loop that is not damaging to the healthy lumen size and/or shape of the lumen. In one aspect, the configuration controls the width of the loop to be about half the diameter of the tissue lumen or less. In one aspect, the configuration controls the width of the loop relative to the lumen diameter. In one aspect, the configuration controls the width of the loop relative to the lesion.

The distal-most portion of the loop is referred to herein as the leading distal end, or leading portion. The leading distal end of the loop can be configured in accordance with the principles of the invention to have a size and shape that are optimized for a particular application. For example, the leading distal end can be pointed, rounded, convex, or concave depending on the shape and hardness of the lesion to be interrogated.

The leading distal end of the loop can be configured to come into contact with the lesion. The distal end of the loop can be generally configured with a curvature of various types, some of which are shown in the drawings and discussed below. In one aspect, the leading distal end can be configured to be pointed, providing a smaller surface area for contacting the occlusion as compared to a loop having a rounded leading end. When the leading distal end contacts the lesion, the pointed leading distal end concentrates a force applied to the lesion over a smaller area of the lesion than a rounded leading distal end would.

The loop portion of the crossing wire can be pre-formed such that the leading distal end of the loop has a predetermined configuration. For example, the crossing wire can assume a looped or bent shape even when no external forces are acting on it. When no forces are acting on the loop, the configuration of the loop can be referred to as a "relaxed" or steady-state configuration. The fact that the loop is pre-formed helps maintain the narrow width of the loop, because the crossing wire itself will provide a counter-force when the loop is expanded beyond its pre-formed width. For example, when the leading distal end of the loop is brought into contact with a lesion and additional force is applied to the crossing wire, if the lesion resists the applied forces, the loop may begin to expand. However, the crossing wire itself will provide tensile forces that resist expansion of the loop beyond its preformed width. The widest portions of the loop can contact the vessel wall, and can stabilize the loop with respect to the vessel wall, such as the arterial wall.

In addition to the loop configuration contemplated in its basic form as discussed above in various aspects and configurations, the loop can further be configured to include more complex loop configurations. The additional loop configurations can have a single loop configuration as the basis of the loop configurations. The loop can be configured to allow for twisting and/or wrapping of the loop during use.

The loop alone and/or in combination with the catheter can be configured to be adaptable and/or controlled during use by methods and techniques contemplated herein. In one aspect, during use of the CTO crossing device, the operator, such as a physician, can control the crossing wire by displacement, for example, such as by rotation and/or twisting. The operator can twist a portion of the wire proximal to the catheter, causing a portion of the wire extending beyond the distal end of the catheter to become intertwined with itself. This can prevent the loop from becoming too wide, and also provides axial support for the leading portion of the loop.

The present device enables the physician to control the width of the loop, thereby enhancing the safety and efficacy of the procedure. Some configurations of the invention also include a catheter, into which the looped crossing wire is disposed. By disposing the wire inside the catheter, the amount of bowing that the wire can undergo is limited. If the wire begins to bow inside the catheter, the catheter wall redirects the lateral forces so that they extend along the length of the catheter, and toward the leading distal end of the loop.

A device for crossing a lesion according to some embodiments of the invention is shown in FIG. 1A. The device 100 includes a catheter 102 including a lumen 104, the catheter 102 having a proximal end 106 and a distal end 108. The device also includes a crossing wire 110 configured to pass through lumen 104, the crossing wire 110 including a loop 112 at a distal end of the crossing wire 110, the loop 112 having a relaxed state such that opposite sides 114, 116 of the loop form an angle that is less than 180 degrees, and the loop 112 having a leading portion 118 configured to interrogate the lesion.

Figure 1B:
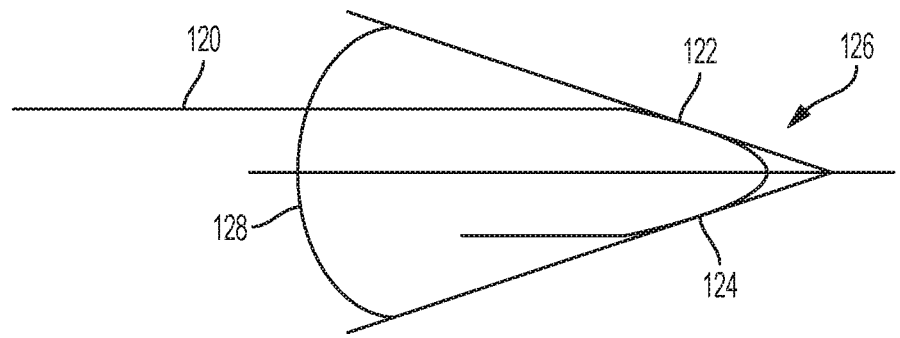
FIG. 1B shows a crossing wire in a relaxed state.

The term "relaxed state" is intended to mean a state of the crossing wire when no external forces are exerted on it. For example, FIG. 1B shows a crossing wire 120 in a relaxed state. The opposite sides 122, 124 of the loop 126 can form an angle 128. The angle can be less than 180 degrees. In one aspect of the invention, the angle is between about 90 and about 45 degrees. In one aspect of the invention, the angle is between about 60 and about 30 degrees. The angle will influence the width of the looped portion of the crossing wire. A crossing wire with opposite sides that form an angle of 90 degrees in a relaxed state will form a wider loop than a crossing wire with opposite sides that form an angle of 45 degrees in a relaxed state. The angle may be chosen based on the diameter of the vessel, with smaller angles corresponding to smaller vessels and larger angles corresponding to larger vessels. Further, loops forming a wider angle may be chosen for navigating the true lumen of a vessel during a CTO crossing procedure, while loops forming a narrower angle may be chosen for navigating the subintimal region of the vessel, if the CTO cannot be crossed with the loop remaining in the true lumen.

Figure 2:
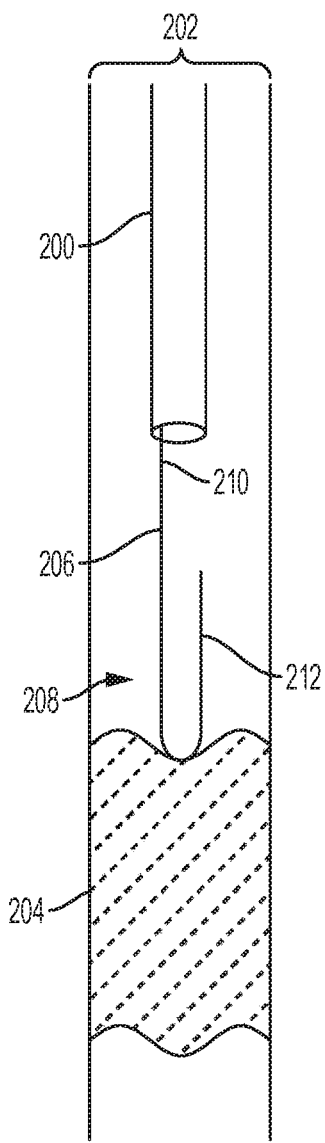
FIG. 2 shows a device according to one aspect of the invention inside a vessel lumen with a CTO.

FIG. 2 shows a catheter 200 inside a vessel lumen 202. A CTO 204 blocks the lumen 202. A CTO wire 206 is shown extending beyond the distal end of the catheter 200. The CTO wire 206 has a loop 208 that forms the distal end of the CTO wire 208. The loop 208 can come into contact with the CTO 204, and can be used by the physician to perform microdissection of the CTO, opening the vessel and creating a path for a guide wire or other device if further treatment is required. The physician my use multiple looped CTO wires to cross the CTO. For example, the physician may use a first looped CTO wire from an antegrade approach and a second looped CTO wire from a retrograde approach.

The CTO wire can undergo structural formation such that, when no forces are applied to the wire, the wire assumes the configuration or shape as shown, where a portion of the wire doubles back. For example, in FIG. 2, the CTO wire 206 has a main shaft 210, a loop 212, and a second shaft 212 that doubles back toward the catheter 200. The wire including the double-backed portion may form a V-shape, a U-shape, a W-shape, or an M-shape, for example. These shapes are provided as examples, and the embodiments of the invention are not limited to these shapes. The wire including the doubled-back portion may be referred to herein as "looped." Loop 208 can be pre-formed, and can have shape memory characteristics. The shape memory characteristics allow the loop to resist forces that would cause the loop to become wider. For example, if the loop 208 is pre-formed to have a particular width, when a force is exerted on the loop that would cause the width of the loop to increase, tensile forces in the wire will resist the lateral forces, helping maintain the predetermined width of the loop. The loop 208 can be passable through the catheter and can assume its relaxed configuration in whole or in part for use.

The structural formation of the wire can be accomplished by a variety of method, for example, by forming the wire to have a looped shape during its original manufacture, or by applying heat and shaping forces to the wire after its initial formation. Once the wire has undergone structural formation, the wire maintains its structural formation when it is in a relaxed configuration, meaning that no forces are applied to it. When forces are applied to the wire that would change the configuration of the wire, the tensile forces in the wire resist the change. However, the wire may still flex and bend due to the applied forces.

Figures 3A, 3B, 3C, 3D, 3E:
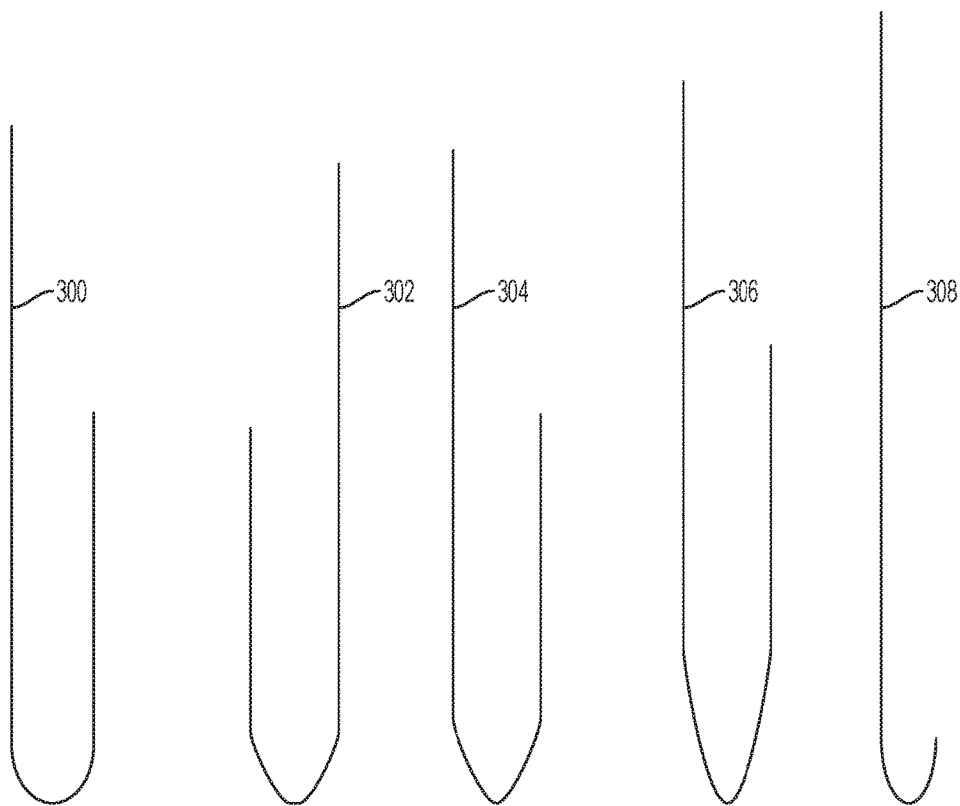
FIG. 3A shows a first example of a looped wire.
FIG. 3B shows a second example of a looped wire.
FIG. 3C shows a third example of a looped wire.
FIG. 3D shows a fourth example of a looped wire.
FIG. 3E shows a fifth example of a looped wire.
Figure 3F:
FIG. 3F shows a fifth example of a looped wire.
Figure 3G:
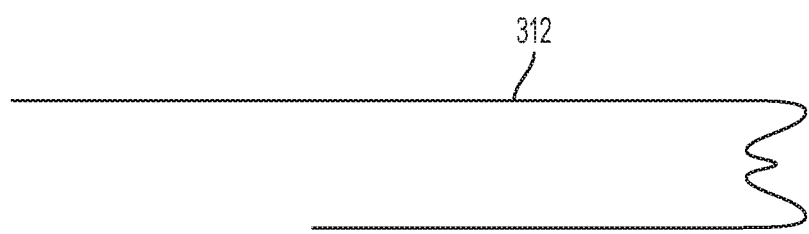
FIG. 3G shows a fifth example of a looped wire.

FIGS. 3A-3G show various configuration of looped wires. Each configuration may be a result of the structural formation of the wire, and may be the relaxed configuration of the wire. In FIG. 3A, the wire 300 has a broad loop. In FIG. 3B, the wire 302 has a broad loop with a flattened tip. In FIG. 3C, the wire 304 has a broad loop with a pointed tip. In FIG. 3D, the wire 306 has an elongated loop with a narrow tip. In FIG. 3E, the wire 308 has a broad loop with one end of the wire located very close to the loop. In FIG. 3F, the wire 310 has a peaked loop. This loop may be used to interrogate a concave lesion. In FIG. 3G, the wire 312 has an inverted loop. This loop may be used to interrogate a convex lesion. A physician may select a particular wire based on the shape and density of the lesion.

According to one aspect of the invention, the crossing wire has a short side on one side of the loop, and a long side on the other side of the loop. The long side of the loop can be disposed within a catheter, while the short side may be disposed within the catheter, or outside of the catheter. According to one aspect of the invention, the short side has a length between about 10 mm and about 70 mm. According to one aspect of the invention, the short side has a length between about 30 mm and about 50 mm. According to one aspect of the invention, the short side has a length of about 40 mm. According to one aspect of the invention, both sides of the loop are the same length.

Figure 4:
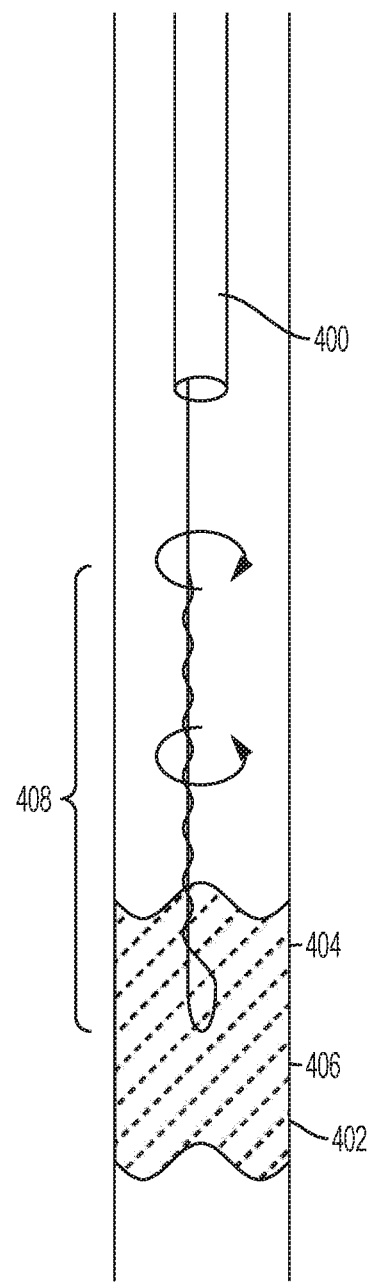
FIG. 4 shows a device according to one aspect of the invention inside a vessel lumen with a CTO where the device has begun to pass into the CTO lesion.

FIG. 4 shows how the looped wire can be used to cross a lesion according to one aspect of the invention. A physician guides the catheter 400 through the vessel until it is within a few millimeters of the lesion 402. The catheter 400 has a crossing wire 404 that is at least partially disposed inside the catheter or passed through the catheter. The crossing wire 404 has a length such that it can be grasped by the physician proximal to the catheter 400, and can simultaneously extend beyond the distal end of the catheter 400. Once the catheter 400 is in position, the physician then extends the crossing wire 404 beyond the distal end of the catheter 400, toward the lesion 402.

The crossing wire 404 has a pre-formed loop. For example, the pre-formed loop may have a relaxed configuration with a primary shaft, a secondary shaft, and a loop portion between the primary and secondary shafts. The primary and second shafts may be separated by a space, as shown in FIGS. 3A-3G. The physician extends the crossing wire 404 until the leading distal end 406 contacts the lesion 402. Once the leading distal end 406 contacts the lesion 402, the physician may probe the lesion with the leading distal end 406. Further, the physician may grasp the crossing wire 404 proximal to the catheter 400, and begin to twist the wire. The two sides of the pre-formed loop begin to twist around themselves, forming a twisted loop 408, as shown in FIG. 4. The twisted loop 408 can have a higher resistance to bending than a conventional CTO wire, allowing the physician to exert greater force on the lesion 402 than would be possible with a conventional CTO wire, while maintain a loop whose width does not exceed the width of the vessel. The physician may continue twisting the wire as he or she applies pressure on the lesion 402, thereby entering into the lesion 402, as shown in FIG. 4. The device entering into the lesion can be referring to as drilling into the lesion. In this way, the physician may use the wire to perform repetitive microdissection of the lesion 402, creating a clear path.

FIGS. 5A-5D show a crossing wire in various configurations. Each of the configurations shown in FIGS. 5A-5D may be used to interrogate and/or cross a lesion. A particular configuration may be chosen based on a variety of considerations, including the size, shape, and hardness of the lesion, for example. The wire may be preformed to have a loop, as in FIG. 5A, that can be twisted to obtain the configurations in FIGS. 5B-5D. Alternatively, the wire may be preformed to have a twisted configuration, such as the configurations shown in FIGS. 5B-5D.

Figure 5A:
FIG. 5A shows a device according to one aspect of the invention where the loop is shown in a relaxed state.
Figure 5B:
FIG. 5B shows the device of FIG. 5A, but in another configuration.
Figure 5C:
FIG. 5C shows the device of FIG. 5A, but in another configuration in a sequence of changing configurations from FIGS. 5A to 5B to 5C.
Figure 5D:
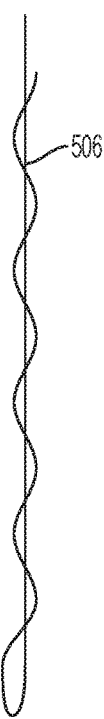
FIG. 5D shows the device of FIG. 5A, but in another configuration in a sequence of changing configuration from FIGS. 5A to 5B to 5C to 5D.

In FIG. 5A, the crossing wire 500 has two ends that are side-by-side. This can be the state of the crossing wire before the physician begins to apply a torque, or twisting motion, to the wire. The crossing wire 500 can be used to advance the wire through a vessel or for pedal loop crossing. In FIG. 5B, the crossing wire 502 has been twisted slightly such that the two sides of the wire have become intertwined. In FIG. 5C, the crossing wire 504 has undergone additional twisting, causing the two sides of the crossing wire to become more tightly intertwined, and causing the loop to become narrower. Intertwining the two sides of the wire increases the stiffness of the wire, providing additional column strength for applying a force on the lesion. The crossing wire 506 in FIG. 5D has undergone even more twisting, causing the two sides of the wire to become even more tightly intertwined, and the loop at the end of the wire to become even narrower. Of the wires 500-506 shown in FIGS. 5A-5D, the tightly intertwined wire 506 will be most resistant to bending, and therefor can be used to apply a strong force to the lesion. Softer lesions may not require such a strong force, and one of the other three wires 500-504 may be sufficient to cross the lesion. The number of rotations and amount of turns or twists in the loop is variable and can be dependent upon the lesion type/hardness. The operator can control the number of twists. The device can be configured to enable the quantity of twists that the crossing wire is capable of forming.

FIGS. 6A-6D show a device in one aspect of the invention positioned in the vasculature with a CTO. The physician begins by obtaining arterial or venous access, and then placing a sheath in the artery or vein. The physician may image the region of interest, for example, using an angiogram, to determine the position of the CTO. As shown in FIG. 6A, the physician may then guide the catheter 600 into close proximity of the lesion 602. The physician then extends the crossing wire 604 beyond the distal end of the catheter 600 until a leading portion 606 of the loop 608 at the distal end of the crossing wire 604 engages the lesion 602.

According to one aspect of the invention, the crossing wire 604 has main shaft 610 on one side of the loop 608 and a secondary shaft 612 on the other side of the loop 608. One or both of the main shaft 610 and the secondary shaft 612 extend back into the catheter 600. At least one of the shafts extends the length of the catheter so that it can be manipulated by the physician. Herein, the shaft that is manipulated is referred to as the "main shaft," though in some configurations of the device the physician may manipulate both shafts. In FIGS. 6A-6D, the main shaft 610 extends through the catheter 600, while the secondary shaft 612, is shorter, and may not be disposed within the catheter 600 while the physician performs the procedure.

Once the leading portion 606 of the crossing wire 604 contacts the lesion 602, the physician begins twisting the main shaft 610 of the crossing wire 604, as shown in FIG. 6B. The secondary shaft 612 becomes intertwined with the main shaft 610, providing column strength to the crossing wire 604, and causing the loop 608 to become narrower. The physician continues twisting the main shaft 610 and applying pressure until the loop 608 crosses the lesion 602, as shown in FIGS. 6C and 6D.

While the physician is applying pressure to main shaft 610, the lesion 602 may resist the force of the distal portion 606 of the loop 608. The axial forces applied by the physician may then be redirected laterally, causing the loop 608 to flex. However, because the loop 608 is formed to have a predetermined width in its relaxed configuration, the loop 608 will resist axial forces that would cause it to become wider than the width of the vessel. Further, by twisting the main shaft 610 and thereby intertwining the main shaft 610 with the secondary shaft 612, the physician maintains the width of the loop to be narrower than the width of the vessel.

The physician may twist the main shaft 610 in a single direction, or may rotate the wire back and forth to erode the lesion 602. According to one aspect of the invention, the physician twists the main shaft 610 until the crossing wire 604 has about three or four nodes, or crossing points, in the loop 608. Additional nodes may decrease the resistance of the wire to lateral forces. If the nodes do not remain in a straight line when lateral forces are applied, the loop 608 may collapse, and the wall of the vessel could rupture.

Figures 20A, 20B, 20C:
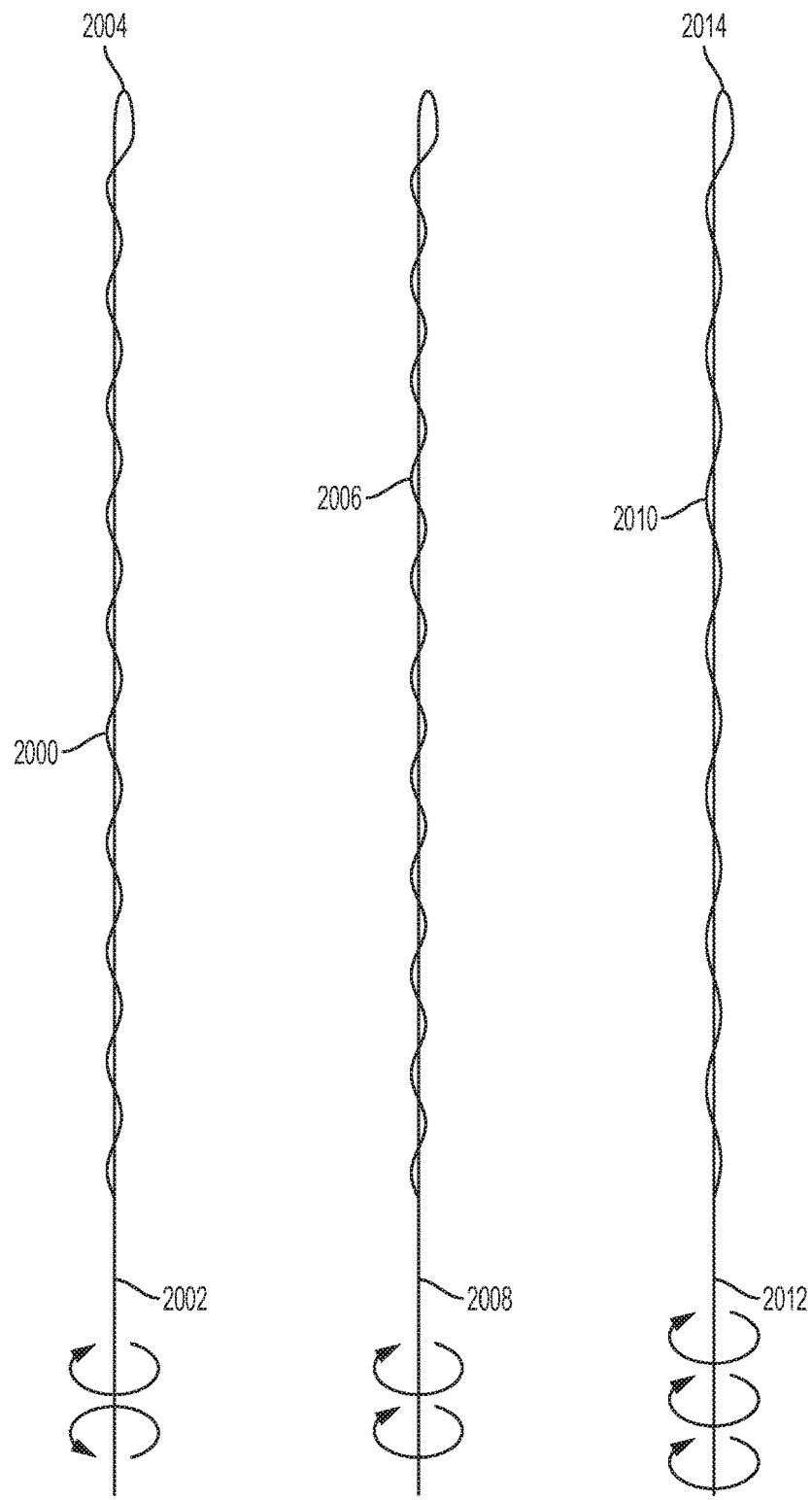
FIG. 20A shows a crossing wire in a loosely twisted configuration.
FIG. 20B shows a crossing wire in a moderately twisted configuration.
FIG. 20C shows a crossing wire in a stiff configuration.

FIGS. 20A-20C show wires in three twisted configurations. In FIG. 20A, the secondary shaft 2000 is loosely twisted around the primary shaft 2002. The primary shaft 2000 can be alternately twisted clockwise and counter-clockwise to maintain the loosely twisted configuration as the distal tip 2004 contacts and crosses the CTO. The left and right rotations can be a point of variation between 0° and 360°. If the primary shaft 2002 is initially twisted in a clockwise direction to obtain the loosely twisted configuration, additional clockwise rotation will tighten the wire and increase the crossing force applied by the distal tip 2004 of the CTO crossing wire on a lesion.

The 0°-360° rotation can be used as a back and forth motion or a continuous clockwise (or counter-clockwise) rotation. The rotation of the wire is at the discretion of the user and may depend on the force required to cross the CTO. If a greater force is required, the user may twist the primary shaft in one direction more than in the other direction to increase the stiffness of the wire, thereby increasing the force that can be applied to the CTO by the distal tip.

In FIG. 20B, the secondary shaft 2006 is moderately twisted around the primary shaft 2008 to form a configuration with moderate stiffness. The CTO wire is kept in moderate configuration by rotating the primary shaft 2008 more in one direction than the other direction. The user can rotate clockwise and counter-clockwise as many times as desired as long as there is a surplus of rotations in one of the directions to maintain a moderate or higher stiffness. The user can continuously rotate the primary shaft 2008 until the desired target goal of the wire tip crossing force is achieved.

In FIG. 20C, the secondary shaft 2010 is tightly twisted around the primary shaft 2012 to form a configuration with high stiffness. The CTO crossing wire configuration is kept stiff by increasing the rotations in favor of one direction over the other. If the primary shaft 2012 is initially twisted in the clockwise direction, additional clockwise rotations will increase the stiffness, while counter-clockwise rotations will decrease the stiffness. Additional clockwise rotation of the primary shaft 2012 leads to an incremental increase in the amount of force that the distal tip 2014 of the wire is able to exert on a lesion. Continuous clockwise rotation leads to a tight bond between the primary shaft 2012 and the secondary shaft 2010, providing additional support for the distal tip 2014. Once the primary shaft 2012 is sufficiently twisted such that the wire has the stiff configuration, the user may rotate the primary shaft 2012 clockwise and counter-clockwise. The user may maintain the stiff configuration during these rotations as long as the counter-clockwise rotations do not exceed the clockwise rotations. The increased stiffness is not permanent. It can be reversed, or the force applied by the distil tip 2014 on the lesion can be changed, by rotating the primary shaft 2012 counter-clockwise.

The distal tip 2014 can have a shape that is influenced by the twisting of the primary shaft 2012 and secondary shaft 2010. Rotating the primary shaft 2012 to obtain a stiff configuration may also narrow the loop and reduce the angle formed by the two sides of the loop. Rotating the primary shaft 2012 in the opposite direction will cause the loop to become broader, increasing the angle between the two sides of the loop. The loop can thus have any configuration desired by the user.

Figures 21A, 21B:
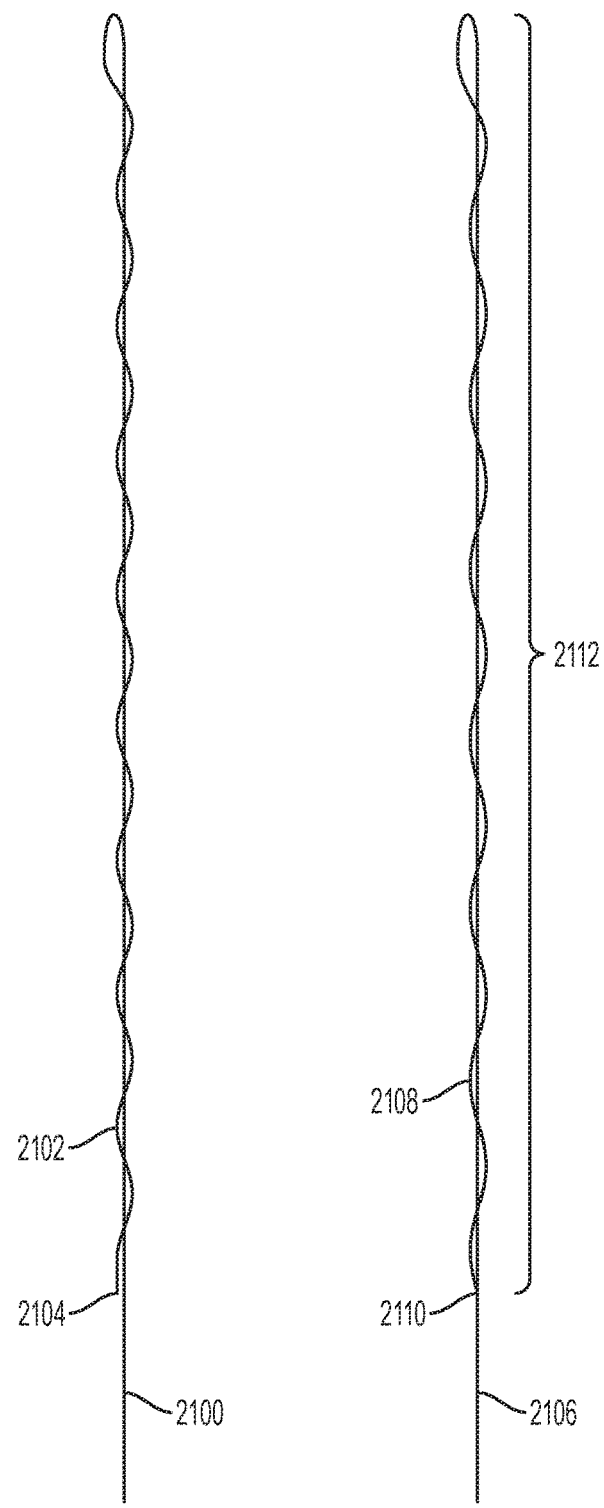
FIG. 21A shows a crossing wire with a secondary shaft that is not connected to the primary shaft at the proximal tip of the secondary shaft.
FIG. 21B shows a crossing wire with a secondary shaft that is connected to the primary shaft at the proximal tip of the secondary shaft.

The secondary shaft 2010 may have different configurations, such as a free tip, or a welded or connected tip. FIG. 21A shows a wire having a primary shaft 2100 and a secondary shaft 2102, where the proximal tip 2104 of the secondary shaft 2012 is free, i.e., not welded to the primary shaft 2100. FIG. 21B shows a wire having a primary shaft 2106 and a secondary shaft 2108, where the proximal tip 2110 of the secondary shaft 2008 is welded or connected to the primary shaft 2106. The secondary shaft 2108 in the welded configuration may be twisted around the primary shaft 2106 prior to welding, or may be substantially parallel to the primary shaft 2106 when the proximal tip 2110 is welded to the primary shaft 2106. Both free and welded tips can have a similar secondary shaft configuration.

The configuration is not affected by the length of the secondary shaft, which can have a variety of lengths. The length 2112 of the secondary shaft 2108 is indicated in FIG. 21B. The length of the secondary shaft 2108 can be configured based on the required stiffness of the wire. The length of the secondary shaft 2108 can therefore vary from just a looped tip to extending the entire length of the primary shaft 2106. The wire can have a pre-formed loop at the distal tip, and the secondary shaft 2108 may or may not be twisted around the primary shaft 2110 while the CTO crossing wire is in a relaxed state, i.e., before the user has begun to rotate the primary shaft 2106. The variations in the wire provide the variations in the force and support needed to cross a lesion in the coronaries or peripheral arteries and veins.

FIGS. 7A-7D show various configurations of a crossing wire. FIGS. 7A-7D demonstrate how the characteristics of the crossing wire can be varied, depending on the desired application. For example, crossing wire 700 in FIG. 7A has a narrower loop 702 than the loop 706 of the crossing wire 704 in FIG. 7B. The secondary shaft 708 of wire 700 is shorter than the secondary shaft 710 of the crossing wire 704. A longer secondary shaft can provide more support to the main shaft, enabling a higher force to be applied on a lesion by the loop without the wire bending or buckling. The crossing wire can be configured to bend at a particular point, which can influence the width of the loop. For example, crossing wire 712 in FIG. 7C can be configured to bend at one of a variety of points 714-722. Positioning the bending point farther from the leading portion 724 of the loop can result in a wider, longer loop, while positioning the bending point closer to the leading portion of the loop can result in a narrower, shorter loop. The position of the bending point can be determined by the structure of the wire, for example, by having different thicknesses along the length of the wire or by having parts of the wire made from different materials to make some portions of the wire more flexible than others. In one aspect of the invention, the distance from the leading portion 724 of the loop to the first node 734 is between about 1 mm and about 40 mm. In one aspect of the invention, the distance from the leading portion 738 of the loop to the distal end of the catheter is between about 3 mm and about 40 mm.

Figures 7A, 7B, 7C, 7D:
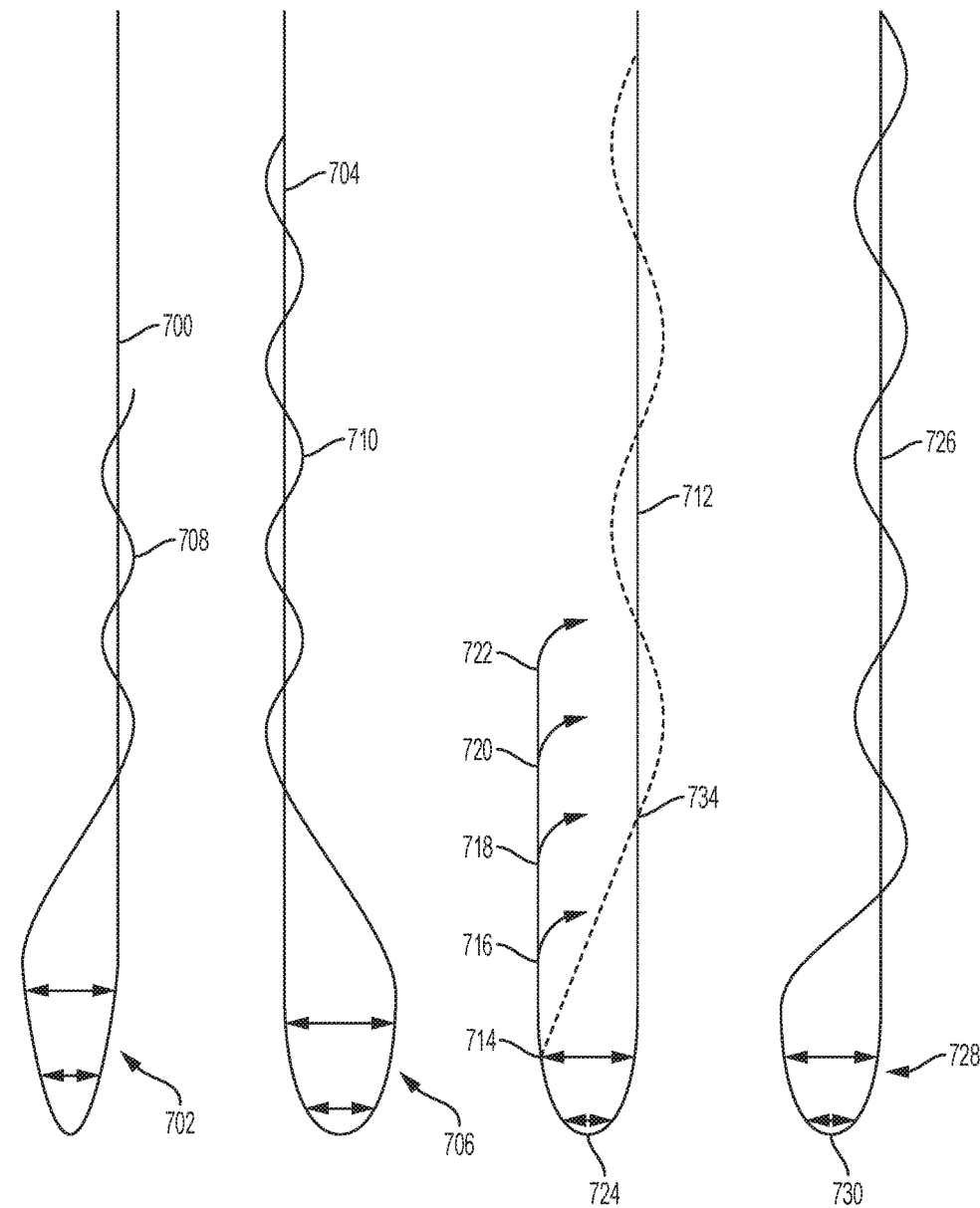
FIG. 7A shows a crossing wire configured in one aspect of the invention.
FIG. 7B shows a crossing wire configured in another aspect of the invention.
FIG. 7C shows a crossing wire configured in another aspect of the invention.
FIG. 7D shows a crossing wire configured in another aspect of the invention.

As shown in FIG. 7A, the wire in some configurations can have a first loop portion 736 that increases in width from the leading distal end 738 to a maximum width 740. The wire includes a second loop portion 742 the decreases in width from the maximum width 740 to a first node 744. The wire includes a tail portion 746 distal to the first node 744. The primary shaft 700 and secondary shaft 708 may form additional nodes in the tail portion 746.

The crossing wire can have varying stiffness along its length. A particular stiffness is chosen based on the application. The crossing wire can include markers that indicate the proper position of the wire for a particular stiffness. Occlusions providing mild resistance can be crossed with a less stiff portion of the wire, while severe occlusions can be crossed with the stiffest portion of the wire. According to one configuration, the crossing wire has three different stiffness values along its length.

The crossing wire 726 in FIG. 7D has a wider loop 728 with a more blunt leading portion 730 than the crossing wires illustrated in FIGS. 7A-7C. The crossing wires illustrated in FIGS. 7A-7D are provided to highlight various characteristics of the crossing wire that can be altered or manipulated to create different configurations of the crossing wire. Some characteristics of the crossing wires shown in FIGS. 7A-7D may be interchanged and/or combined, and the aspects of the invention are in no way limited to the configurations shown in FIGS. 7A-7D.

Figure 18:
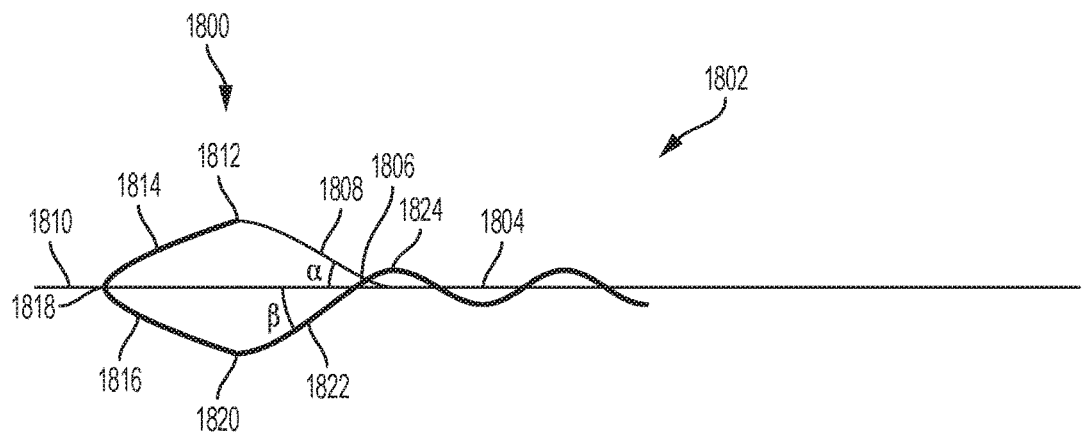
FIG. 18 shows a crossing wire in a twisted configuration.

FIG. 18 shows a crossing wire in a twisted configuration. The crossing wire has a shape similar to that of a sperm, with a head 1800 and a tail 1802. The primary shaft 1804 is bent at the base 1806 of the head 1800, and the first head portion 1808 forms an angle α with respect to the axis 1810 of the primary shaft 1804. The first head portion 1808 may be substantially straight until the first transition point 1812. The wire then bends back toward the axis 1810, forming second head portion 1814. Second head portion 1814 may be substantially straight, or may gradually bend. The second head portion 1814 transitions to a third head portion 1816 at a leading distal end 1818 of the wire. The second head portion 1814 and third head portion 1816 may form a rounded leading distal end, a pointed leading distal end, or any other leading distal end configuration. The third head portion 1816 extends from the leading distal end 1818 back toward the proximal end of the wire. The third head portion extends to the second transition point 1820. The first transition point 1812 and the second transition point 1820 may be the locations where the wire forming the head 1800 is farthest from the axis 1810 of the primary shaft 1804. After the second transition point 1820, the wire has a fourth head portion 1822 that extends back toward the base 1806 of the head 1800. The fourth head portion 1822 may form an angle β with respect to the axis 1810 of the primary shaft 1804. The wire then has a secondary shaft 1824 that wraps around the primary shaft 1804. The secondary shaft 1824 wrapped around the primary shaft 1804 forms the tail portion 1802. According to one configuration, the first head portion 1808 and fourth head portion 1822 are substantially symmetrical. According to one configuration, α and β are substantially equal. In one aspect of the invention, the first head portion 1808 and fourth head portion 1822 form a V-shape (sideways in FIG. 18).

Figure 19A:
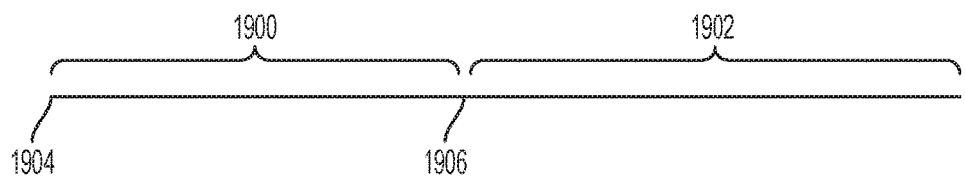
FIG. 19A shows a crossing wire before it has been bent and cured or preformed into a looped configuration.

FIG. 19A shows a crossing wire before it has been bent and cured or preformed into a looped configuration. In one embodiment, the wire has two portions, a first portion 1900 and a second portion 1902, and the two portions do not have the same stiffness. In one configuration, the first portion 1900 is less stiff and more flexible than the second portion 1902. The first portion 1900 can be bent and cured to form the leading distal end of the wire. The first portion 1900 may form a flexible portion of the wire, and can be radiopaque for better visualization under fluoroscopy. The length of first portion 1900 may be between 1 mm and 100 mm. The stiffness of the first portion 1900 may be constant throughout the first portion 1900, or may gradually increase from the tip 1904 of the first portion 1900 to the junction 1906 with the second portion 1902.

The second portion 1902 forms the primary shaft of the crossing wire. The second portion 1902 may also form a portion of the loop when the crossing wire is bent into a looped configuration. The second portion 1902 of the CTO wire may not be radiopaque, and may be stiffer than the first portion 1900. The second portion 1902 can allow the first portion 1900 to loop around the second portion 1902 with added stability and push ability due to the double wire support.

Figure 19B:
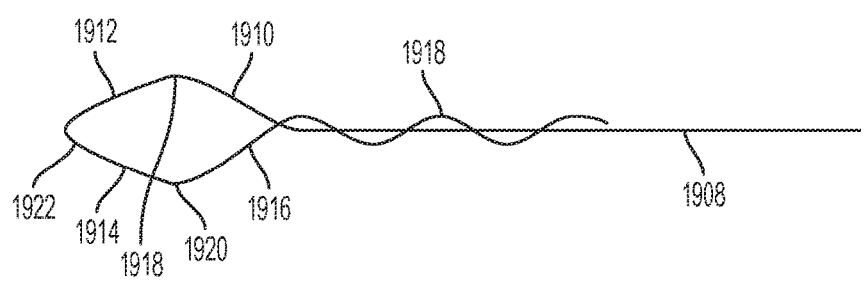
FIG. 19B shows a crossing wire in another twisted configuration.

FIG. 19B shows a crossing wire in a twisted configuration. The primary shaft 1908 and first head portion 1910 are formed from the second portion 1902 in FIG. 19A, while the remaining head portions 1912-1916 and the secondary shaft 1918 are formed from the first portion 1900 in FIG. 19A. The wire may transition from the stiffer second portion 1902 to the more flexible first portion 1900 at the transition point 1918. Alternatively, the wire may transition from the stiffer second portion 1902 to the more flexible first portion 1900 at other positions in the loop 1920.

The second head portion 1912 and third head portion 1914 form the leading distal end 1922 of the crossing wire, and can form a variety of angles and have a variety of configurations. The leading distal end 1922 can have the flexibility to conform to a CTO cap. The wire forming the leading distal end 1922 can also have micro-skives in it to help weaken the CTO cap without impacting the vessel wall.

The secondary shaft 1918 can wrap around the primary shaft 1908, forming a tail that adds propulsion value and stiffness to the leading distal end 1922 of the crossing wire. As the tail becomes more tightly wrapped around the primary shaft 1908, for example, by twisting the primary shaft 1908, the gram weight on the CTO wire and/or crossing device increases along with its ability to penetrate resistant material such as a CTO cap. The primary shaft 1908 can have any diameter deemed fit for a particular CTO crossing. In one aspect, the diameter of the primary shaft 1908 is between 0.09" and 0.35". In one aspect, the diameter of the primary shaft 1908 is one or more of 0.09", 0.14", 0.18", 0.21", 0.24", 0.27", 0.30", 0.33", and 0.35".

Figures 22, 23:
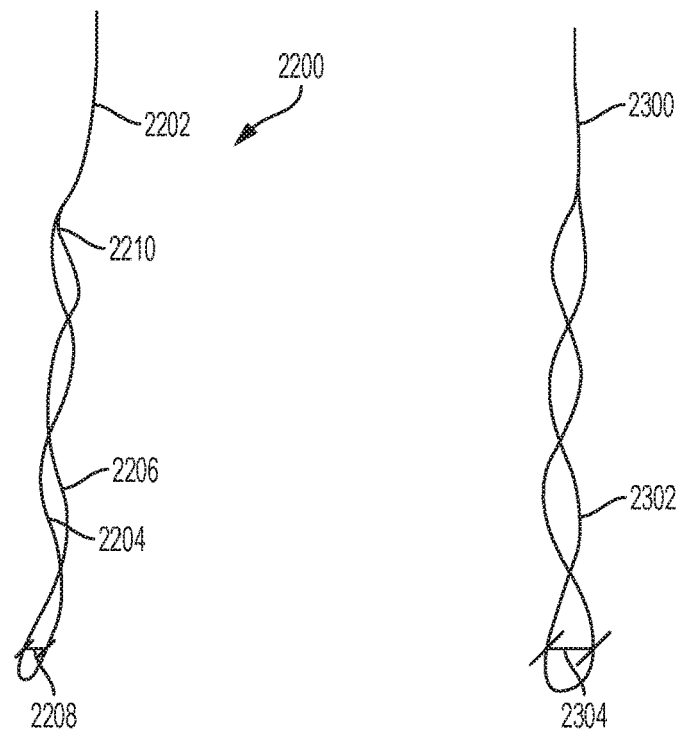
FIG. 22 shows a configuration of a twisted wire forming a loop.
FIG. 23 shows another configuration of a twisted wire forming a loop.

The primary shaft and secondary shaft may have the same diameter along their entire length. Alternatively, the primary shaft may have a first diameter along a proximal portion of the shaft, and a second diameter at the distal portion of the shaft. FIG. 22 shows an example configuration in which the primary shaft 2200 has proximal portion 2202 having a first diameter, for example, 0.35". The primary shaft 2200 has a distal portion 2204 having a second diameter, for example, 0.175". The secondary shaft 2206 may also have the second diameter, for example, 0.175". The combined width 2208 of the loop formed by the distal portion 2204 of the primary shaft 2200 and the secondary shaft 2206 may equal the diameter of the proximal portion 2202 of the primary shaft 2200, for example, 0.35". The diameter values provided herein are solely examples, and the embodiments of the invention are not limited to these values.

The secondary shaft 2206 may be bonded to the distal portion 2204 of the primary shaft 2200. For example, the secondary shaft may be bonded to the primary shaft at the proximal end 2210 of the secondary shaft 2206. The secondary shaft 2206 may be bonded to the distal portion 2204 of the primary shaft 2200 at a plurality of other locations. Alternatively, the secondary shaft 2206 may not be bonded to the distal portion 2204 of the primary shaft 2200. The examples below may also have one or more points at which the secondary shaft is bonded to the primary shaft, or the secondary shaft and primary shaft may not be bonded.

FIG. 23 shows a configuration in which the diameter of the primary shaft 2300 is constant along the length of the primary shaft 2300, and is equal to the diameter of the secondary shaft 2302. For example, the primary shaft and the secondary shaft may each have a diameter of 0.35", while the width 2304 of the loop formed by the primary shaft 2300 and secondary shaft 2302 is twice the diameter of each shaft, for example, 0.70".

Figures 24, 25:
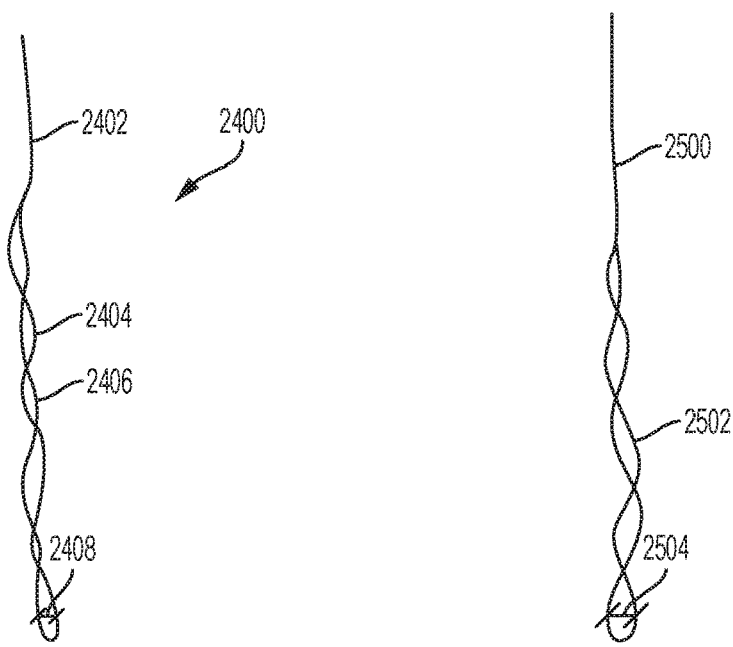
FIG. 24 shows another configuration of a twisted wire forming a loop.
FIG. 25 shows another configuration of a twisted wire forming a loop.

FIG. 24 shows an example configuration in which the primary shaft 2400 has a proximal portion 2402 having a first diameter, for example, 0.18". The primary shaft 2400 has a distal portion 2404 having a second diameter, for example, 0.09". The secondary shaft 2406 may also have the second diameter, for example, 0.09". The combined width 2408 of the loop formed by the distal portion 2404 of the primary shaft 2400 and the secondary shaft 2406 may equal the diameter of the proximal portion 2402 of the primary shaft 2400, for example, 0.18".

FIG. 25 shows a configuration in which the primary shaft 2500 and the secondary shaft 2502 each have the same diameter, for example, 0.18", while the width 2504 of the loop formed by the primary shaft 2500 and secondary shaft 2502 is twice the diameter of each shaft, for example, 0.36". A user may stiffen the wire by rotating the primary shaft 2500 clockwise, for example, and loosen the wire by performing a counter-clockwise rotation, for example, of the primary shaft 2500.

Figures 26, 27:
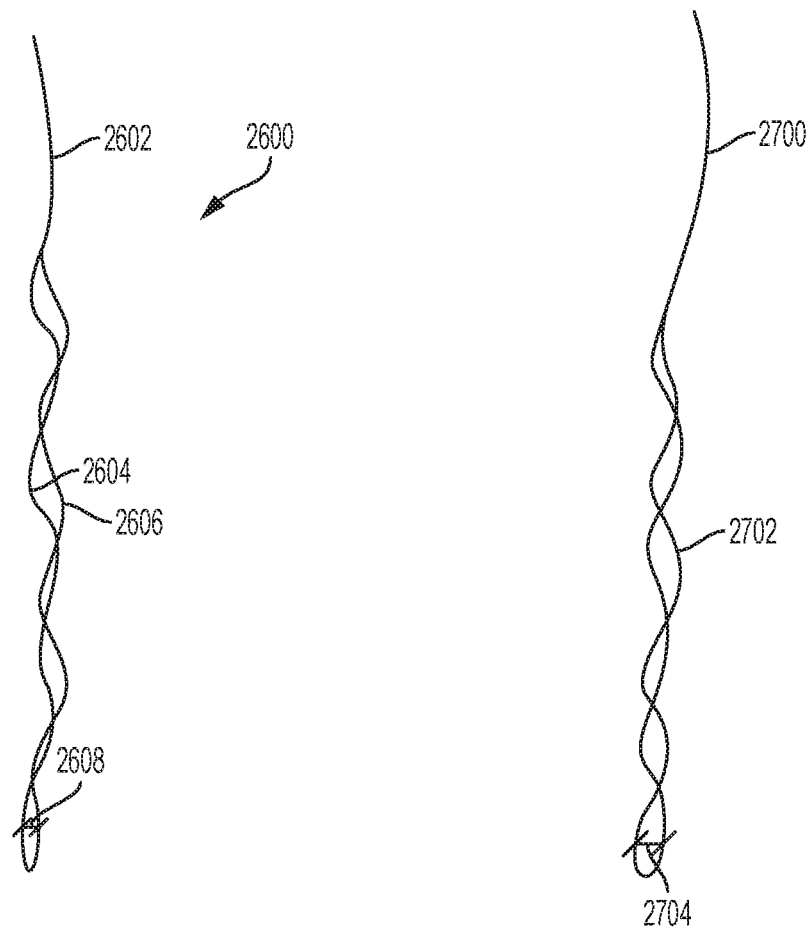
FIG. 26 shows another configuration of a twisted wire forming a loop.
FIG. 27 shows another configuration of a twisted wire forming a loop.

FIG. 26 shows an example configuration in which the primary shaft 2600 has proximal portion 2602 having a moderately stiff body and a first diameter, for example, 0.14". The primary shaft 2600 has a distal portion 2604 having a second diameter, for example, 0.07". The secondary shaft 2606 may also have the second diameter, for example, 0.07". The combined width 2608 of the loop formed by the distal portion 2604 of the primary shaft 2600 and the secondary shaft 2606 may equal the diameter of the proximal portion 2602 of the primary shaft 2600, for example, 0.14".

FIG. 27 shows a configuration in which the primary shaft 2700 and the secondary shaft 2702 may each have a diameter of 0.14", while the width 2704 of the loop formed by the primary shaft 2700 and secondary shaft 2702 is twice the diameter of each shaft, for example, 0.28". The 0.28" loop may be stiffened by tightening the helical distal portion of the primary shaft 2700 and/or the helical secondary shaft 2702 by rotating the primary shaft 2700 clockwise, for example. The stiffness of the 0.28" loop may be reduced by rotating the primary shaft 2700 in the opposite direction, for example, counter-clockwise. The loop in the configuration of FIG. 27 may be stiffer than the loop in the configuration of FIG. 24, because the primary and secondary helical wires forming the loop are thicker relative to the diameter of the proximal portion of the primary shaft than in FIG. 24.

Figure 28A:
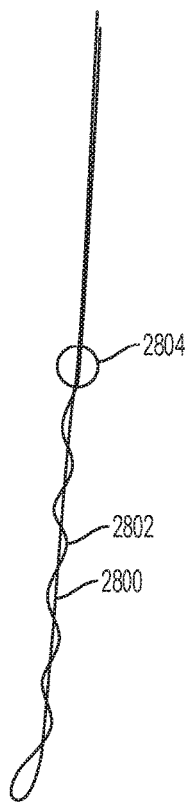
FIG. 28A shows another configuration of a twisted wire forming a loop.
Figure 28B:
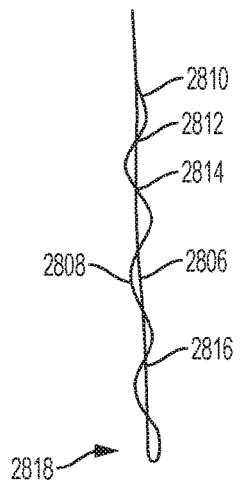
FIG. 28B shows another configuration of a twisted wire forming a loop.

As described above, the primary shaft and the secondary shaft of the wire may or may not be bonded to one another. FIG. 28A shows a configuration in which the primary shaft 2800 is a straight shaft, and the secondary shaft 2802 is a helical shaft that winds around the straight shaft 2800. The proximal end 2804 of the helical secondary shaft 2802 may be independent of, i.e. not bonded to, the primary shaft 2800. FIG. 28B shows a configuration in which the primary shaft 2806 is straight shaft, and the secondary shaft 2808 is a helical shaft. The proximal end 2810 of the helical secondary shaft 2808 is bonded to the primary shaft 2806. The secondary shaft 2808 may be additionally or alternatively bonded to the primary shaft at other points, for example, on or more of the crossing points 2812, 2814, 2816 shown in FIG. 28B. Bonding the primary shaft 2806 to the secondary shaft 2808 increases the stiffness of the wire and the loop 2818 at the distal end of the wire. The helical secondary shaft 2808 may be integrally formed with the primary shaft 2806, or may be separately formed and then bonded to the primary shaft to form a continuous wire, for example, at or near the loop 2818. The helical secondary shaft 2808 may have the same diameter as the primary shaft 2806, or a different diameter. The primary shaft 2806 may also have varying diameters along its length.

Figure 29:
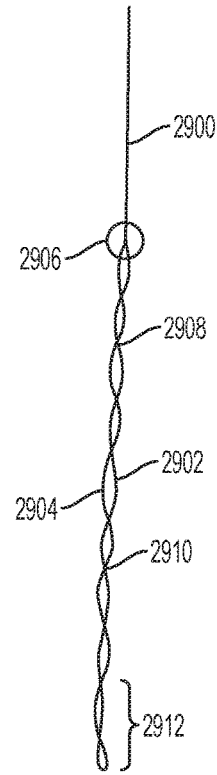
FIG. 29 shows another configuration of a twisted wire forming a loop.

FIG. 29 shows a configuration in which both the distal portion 2902 of the primary shaft 2900 and the secondary shaft 2904 have a helical configuration. The secondary shaft 2904 can be bonded to the primary shaft 2900 at the proximal end 2906 of the secondary shaft 2904, and at other points, for example, points 2908, 2910 along the length of the secondary shaft. The distal tip 2912 may have a shape that can be adjusted by the user, for example by twisting the primary shaft 2900 clockwise or counter-clockwise. The proximal portion of the primary shaft 2900 may be integrally formed with the distal portion 2902 of the primary shaft 2900 and the secondary shaft 2904. Alternatively, the distal portion 2902 of the primary shaft 2900 and the secondary shaft 2904 may be integrally formed, and may be bonded to the proximal portion of the primary shaft 2900 to form a continuous wire. This configuration may be useful when the proximal portion of the primary shaft 2900 has a different diameter than the distal portion 2902 of the primary shaft 2900 and the secondary shaft 2904. The wire may be preformed to have the twisted shape shown in FIGS. 22-29, or the twisted shape may be obtained in situ, for example, by rotating the primary shaft.

Figures 8A, 8B, 8C, 8D:
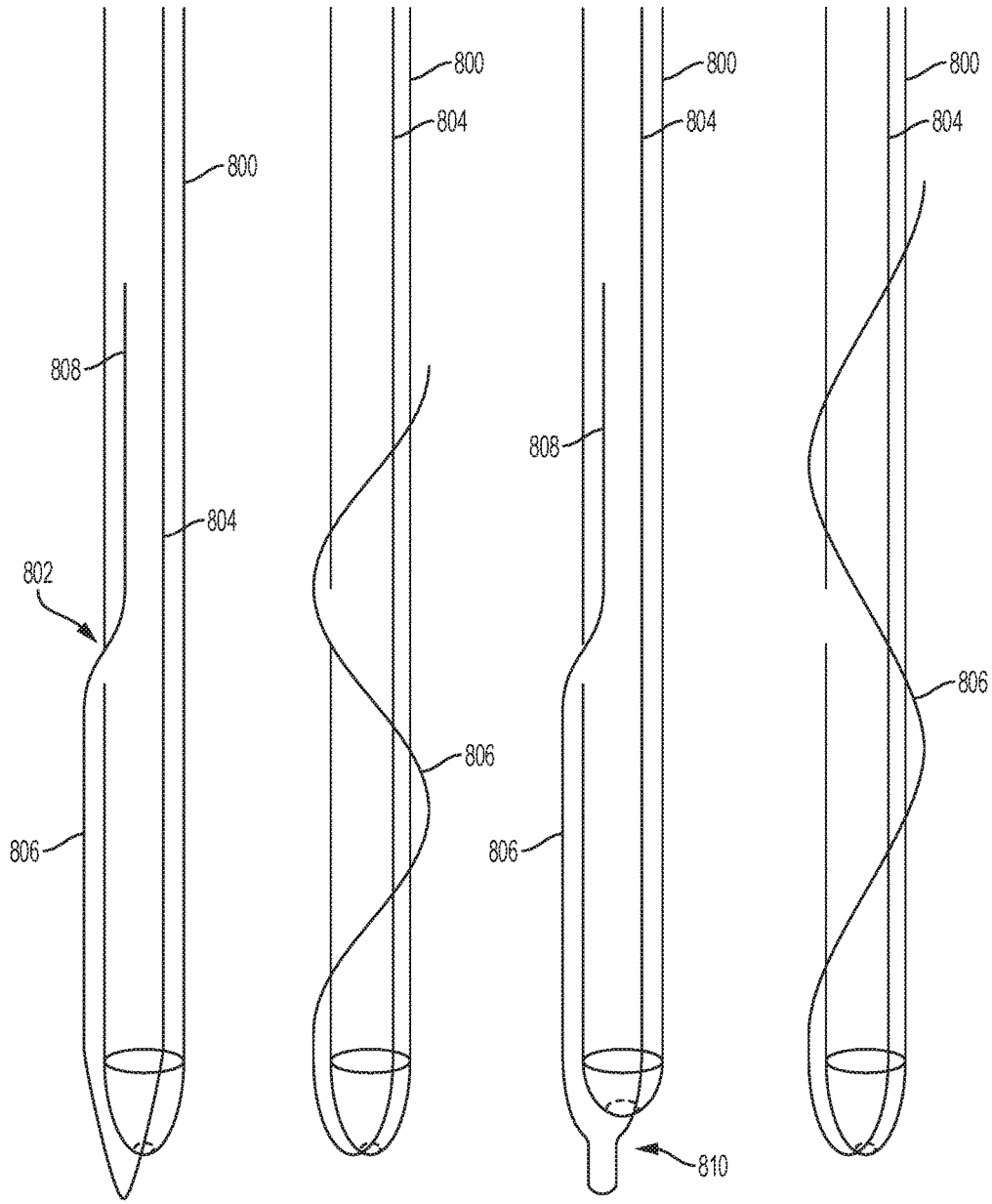
FIG. 8A shows a catheter with a side opening and a crossing wire configured in one aspect of the invention.
FIG. 8B shows a catheter with a side opening and a crossing wire configured in another aspect of the invention.
FIG. 8C shows a catheter with a side opening and a crossing wire configured in another aspect of the invention.
FIG. 8D shows a catheter with a side opening and a crossing wire configured in another aspect of the invention.

In some aspects, the crossing wire is used in conjunction with a catheter. FIG. 8A shows a catheter with a side opening and a crossing wire configured in one aspect of the invention. The catheter 800 includes a hole 802 in a side surface of the catheter 800. As shown in FIG. 8A, the main shaft 804 of the crossing wire is disposed in the lumen of the catheter 800, while the secondary shaft 806 is at least partially disposed outside the lumen. In FIGS. 8B and 8D, a portion 808 of the secondary shaft 806 enters the lumen through the hole 802. In FIGS. 8A and 8C, the secondary shaft 806 wraps around the outside of the catheter 804 without entering the hole 802. The catheter according to one aspect can be prepared with secondary shaft 806 the crossing wire at least partially disposed outside the lumen before the catheter is introduced into the vessel or artery. As show in FIGS. 8A-8D, the loop can have various configurations. For example, the loop can be pointed, rounded, or peaked, as in the loop 810. As would be understood by one of ordinary skill in the art from the configuration of the catheter 800 and crossing wire 806 in FIGS. 8B and 8D, the catheter according to some configurations can be formed without a hole 802, and the secondary shaft 806 can remain outside of the catheter along its length.

Figure 8E:
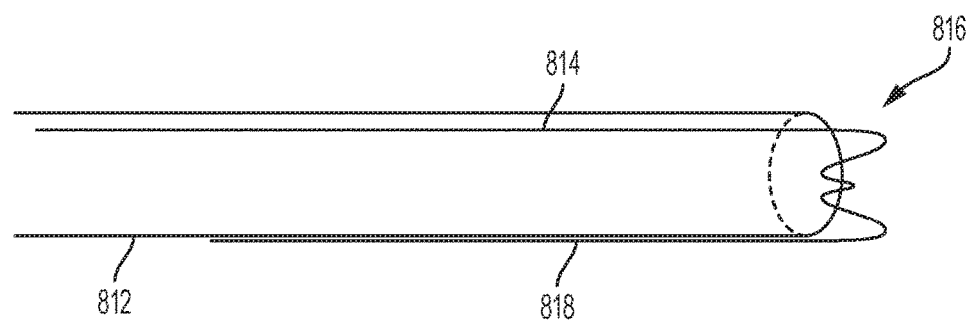
FIG. 8E shows a catheter and crossing wire with an inverted loop configuration according to some embodiments of the invention.

FIG. 8E shows a catheter and crossing wire having another configuration. The main shaft 814 of the crossing wire is disposed within the lumen of the catheter 812, while the secondary shaft 818 is disposed outside the lumen. The crossing wire includes an inverted loop 816.

Figures 9A, 9B, 9C:
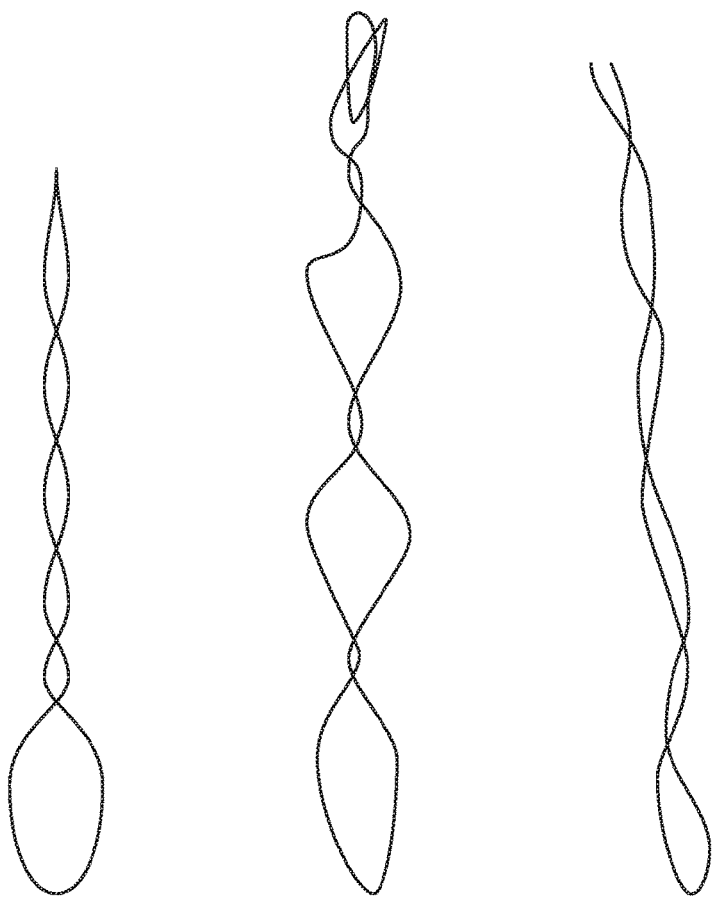
FIG. 9A shows a configuration of a looped crossing wire configured in one aspect of the invention.
FIG. 9B shows another configuration of a looped crossing wire configured in one aspect of the invention.
FIG. 9C shows another configuration of a looped crossing wire configured in one aspect of the invention.

FIGS. 9A-9C shows additional configurations of looped crossing wires according to some aspects of the invention. As shown in FIGS. 9A-9C, the intertwined shafts of the wire may have a variety of shapes, as may the loops.

Figure 10:
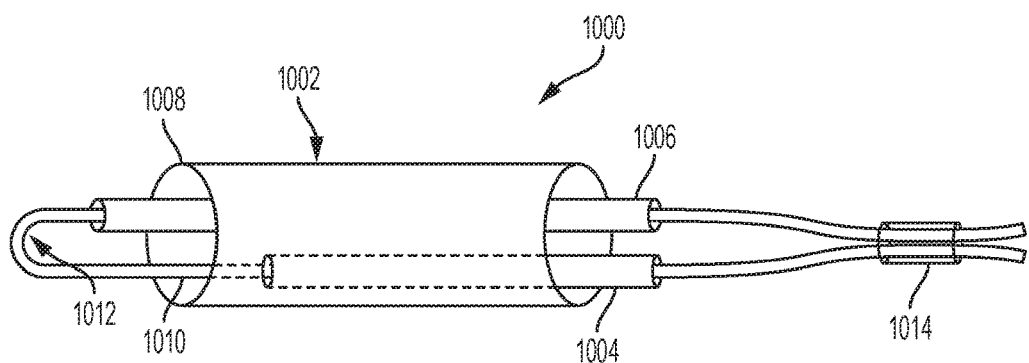
FIG. 10 shows a device configured in one aspect of the invention, in which two additional inner catheters are disposed within the outer catheter.

FIG. 10 shows a device 1000 configured in one aspect of the invention, in which two additional inner catheters 1002, 1004 are disposed within the outer catheter 1002. The inner catheters can be stationary, mobile, or a combination of both. The device 1000 in FIG. 10 has one inner catheter 1004 that is stationary, and one inner catheter 1006 that is mobile. The mobile inner catheter 1006 can be moved longitudinally along the length of the outer catheter 1002, and can even be pushed to extend beyond the distal end 1008 of the outer catheter 1002, as shown in FIG. 10. The mobile inner catheter 1006 can also be manipulated radially around the inside of the outer catheter 1002. As shown in FIG. 10, the crossing wire 1010 passes through the stationary inner catheter 1004 and the mobile inner catheter 1006, and forms a loop, or U-turn, at the distal end of the device 1000. The leading portion 1012 of the loop is brought into contact with the lesion. FIG. 10 also shows a torque device 1014 that can be used to grasp the two wires to prevent them from moving with respect to one another. A physician can use the torque device 1014 to manipulate the crossing wire and loop. For example, once the outer catheter has neared the lesion, the loop can be extended beyond the distal end of the catheter to contact the lesion, and then the physician can twist the torque device 1014 to create one or more figure eight-like segments in the distal portion of the wire.

According to one aspect, a method for crossing a lesion involves moving the portion of the crossing wire 1010 in the mobile inner catheter 1006 with respect to the portion of the crossing wire 1010 in the stationary inner wire 1004. This causes the leading portion 1012 of the loop to undergo a fan-like motion. One side of the loop portion is stationary, while the other side moves in an arc around it. The leading portion 1012 of the loop acts like a sweeping blade that shaves into the lesion.

Figure 11A:
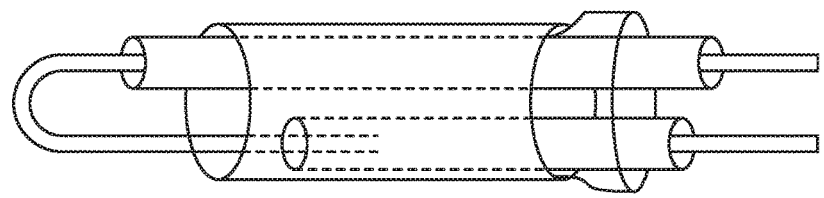
FIG. 11A shows another configuration of a device with two additional inner catheters disposed within the outer catheter.
Figure 11B:
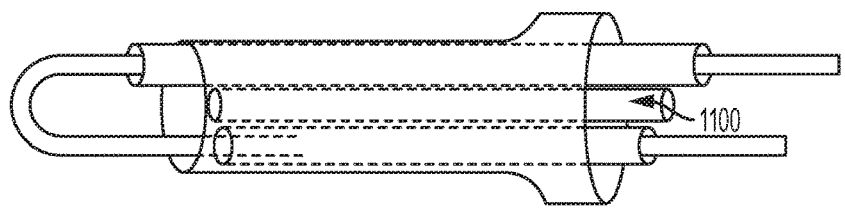
FIG. 11B shows a configuration of a device with three additional inner catheters disposed within the outer catheter.
Figure 11C:
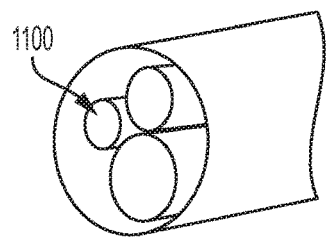
FIG. 11C shows an end of an outer catheter with three catheters disposed therein.

FIG. 11A shows another configuration of a device with two additional inner catheters disposed within the outer catheter. An additional inner catheter can be provided for a conventional and/or additional guidewire. The additional inner catheter 1100 is shown in FIGS. 11B and 11C. The inner support catheters support the looped CTO wire and help manage the portions of the wire. The inner support catheters also provide column strength to prevent buckling of the wire.

Figure 12:
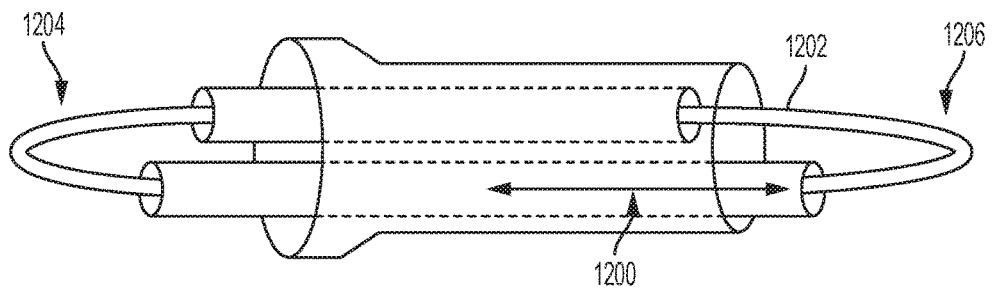
FIG. 12 shows a configuration of a device wherein at least one inner catheter is mobile with respect to the outer catheter.

FIG. 12 shows a configuration of a device wherein at least one inner catheter 1200 is mobile with respect to the outer catheter. The crossing wire 1202 forms a continuous loop at both the distal end 1204 and proximal end 1206 of the device.

Figure 13A:
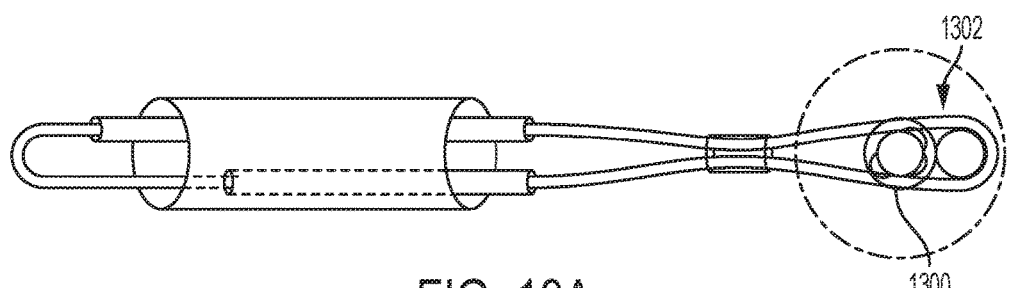
FIG. 13A shows a configuration of a device having a wheel to facilitate twisting of the crossing wire.
Figure 13B:
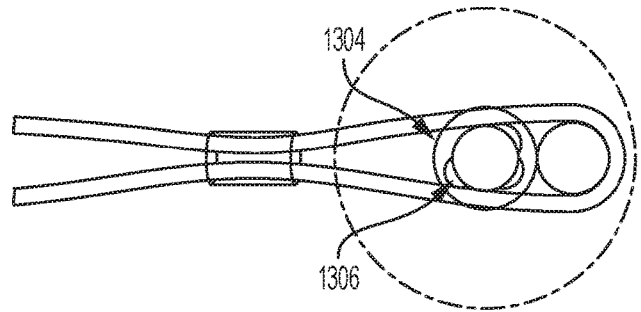
FIG. 13B shows an enlarged image of the wheel of FIG. 13A.

FIG. 13A shows a configuration of a device having a wheel to facilitate twisting of the crossing wire. The wheel 1300 is disposed within the proximal loop 1302 of the crossing wire. The wheel 1300 can facilitate twisting of the crossing wire. FIG. 13B shows an enlarged view of the wheel 1300 of FIG. 13A. The wheel 1300 includes an outer circle 1304 that represents an outer grabber that helps rotate the wire. The semicircles 1306 represent an inner grabber that helps adjust the position of the leading distal end of the loop.

Figure 14:
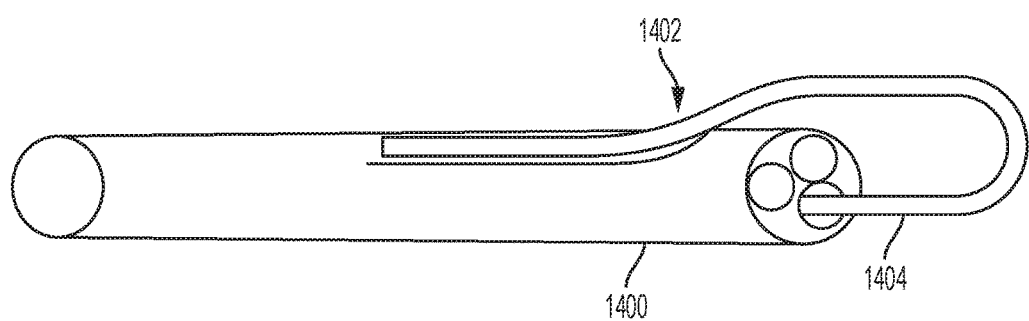
FIG. 14 shows a configuration of a device in which a plurality of catheters are disposed within the outer catheter, and the outer catheter includes a hole in a side surface.

FIG. 14 shows a configuration of a device in which a plurality of catheters are disposed within the outer catheter 1400, and the outer catheter 1400 includes a hole 1402 in a side surface. The crossing wire 1404 exits the distal end of the catheter 1400, and then reenters the lumen of the catheter through the side hole 1402.

Figure 15A:
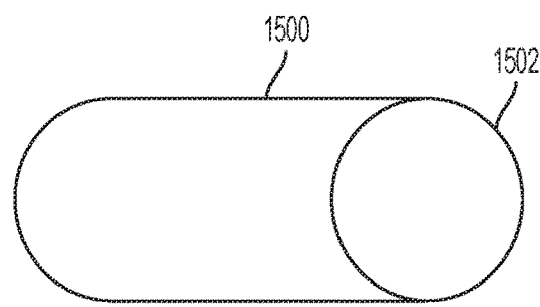
FIG. 15A shows a configuration of a cross-section of a crossing wire.
Figure 15B:
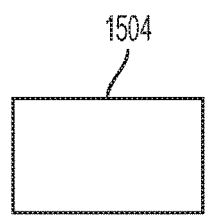
FIG. 15B shows another configuration of a cross-section of a crossing wire.
Figure 15C:
FIG. 15C shows another configuration of a cross-section of a crossing wire.
Figure 15D:
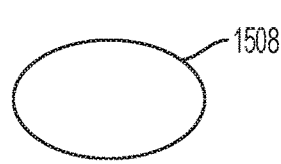
FIG. 15D shows another configuration of a cross-section of a crossing wire.
Figure 15E:
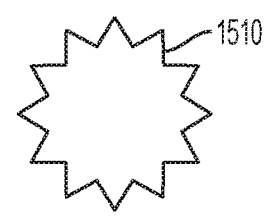
FIG. 15E shows another configuration of a cross-section of a crossing wire.

In some configurations of the device, the crossing wire has a cross-section that is not circular. FIG. 15A shows a crossing wire 1500 having a circular cross-section 1502. However, it may be beneficial to have a cross-section that is not circular, to allow for a smaller surface area of the wire to interrogate the lesion. The cross-section may have a variety of shapes. For example, FIG. 15B shows a first rectangular cross-section 1504, and FIG. 15C shows a second rectangular cross-section 1506. FIG. 15D shows an oval cross-section 1508. FIG. 15E shows a cross-section 1510 with a serrated edge. The serrated edge may be applied to any cross-section to aid the physician in interrogating the lesion.

Figure 16:
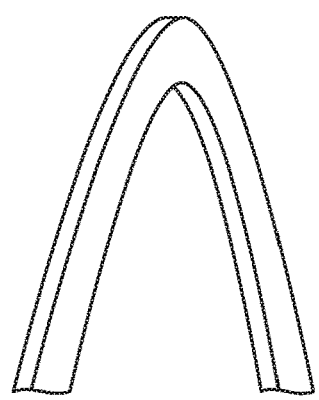
FIG. 16 shows an example of a loop having a rectangular cross-section.

FIG. 16 shows an example of a loop having a rectangular cross-section.

The pre-formed CTO wires can be produced from a single material, and the two sides of the wire and the looped portion can be integrally formed. Alternatively, the sides of the wire may be made from a first material, and the looped portion made be made of a second material, and the two materials may be welded together to form a continuous wire. This enables the side portions of the wire to be formed from a material that has properties that are different from the material properties of the looped portion. For example, it may be beneficial to have the looped portion formed from a material that is more resistant to bending than the material from which the side portions are formed. As an additional example, the sides and looped portion of the wire may all be formed from the same material, but may have different properties that change the compliance of the wire. For example, the wire at looped portion may be thicker or thinner than the wire at the side portions, making the looped portion more or less resistant to bending than the side portions.

Figure 17:
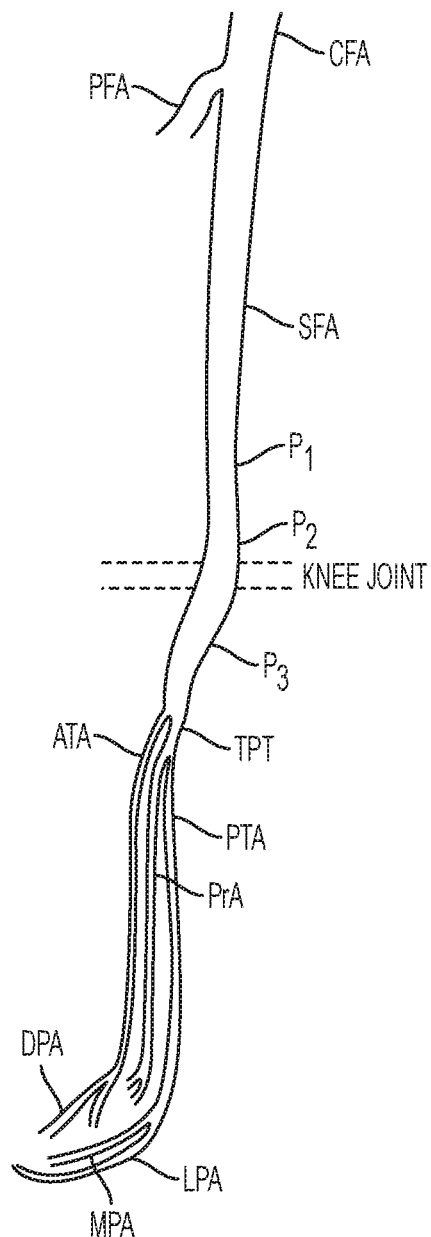
FIG. 17 shows arteries below the knee as an example vasculature in which the device can be used.

Existing CTO crossing devices are too large to be used in the arteries below the knee. The present device can have a size that allows it to be used below the knee, for example, throughout the vasculature illustrated in FIG. 17. The device can be used in vessels having a diameter between 1.5 mm and 30 mm, according to some aspects. According to one aspect, the catheter is a 0.035" catheter. According to one aspect, the crossing wire is a 0.018" wire. The embodiments of the invention are not limited to these dimensions.

The CTO specialty wire can have the same or varying degrees and/or combinations of rigidity and/or column strength so that the loop at the end can be moved in and out to the desired portion/rigidity/strength wire for a particular application. The combination(s) of rigidity can be predetermined.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A device for crossing a lesion in a tissue lumen, comprising:
    a crossing wire configured to pass through a lumen of a catheter, the crossing wire including a loop at a distal end of the crossing wire, the loop having a configuration that prevents a width of the loop from exceeding a width of the tissue lumen, and the loop having a leading portion configured to interrogate the lesion,
    wherein the crossing wire is an elongated wire, the crossing wire having a proximal end controllable by a user,
    wherein the distal end of the crossing wire is configured for positioning in the tissue lumen for crossing a chronic total occlusion, the distal end including the loop, the loop having a pair of lateral opposing portions configured for alignment with a wall of the tissue lumen and the leading portion interconnecting the pair of lateral opposing portions, wherein the loop is configured for crossing the chronic total occlusion,
    wherein the proximal end of the crossing wire forms a portion of a primary shaft of the crossing wire, wherein one of the pair of lateral opposing portions of the loop is directly connected to the primary shaft, and wherein another of the pair of lateral opposing portions is directly connected to a secondary shaft of the crossing wire,
    wherein the crossing wire is configured to have a first configuration when contacting the lesion, wherein the primary shaft and secondary shaft are not intertwined in the first configuration,
    wherein the crossing wire is configured to have a second configuration when penetrating the lesion, wherein in the second configuration the primary shaft and the secondary shaft are intertwined by a first amount and the loop has width that is narrower than a width of the loop in the first configuration,
    wherein the crossing wire is configured to have a third configuration when crossing the lesion, wherein in the third configuration the primary shaft and the secondary shaft are intertwined by a second amount that is greater than the first amount, and the loop has a width that is narrower than a width of the loop in the second configuration and,
    wherein the leading portion of the loop has a concave configuration such that the pair of lateral opposing portions extend distal to a center of the leading portion of the loop.

2. The device for crossing a lesion according to claim 1, further comprising the catheter, wherein the catheter has a proximal end and a distal end.

3. The device for crossing a lesion according to claim 2, wherein the catheter further includes a hole in a side surface of the catheter,
    wherein a first proximal side of the loop is configured to be disposed within the lumen of the catheter, and wherein a second proximal side of the loop is configured to enter the lumen of the catheter through the hole in the side surface of the catheter.

4. The device for crossing a lesion according to claim 2, further comprising:
    a stationary inner catheter disposed within the catheter, the stationary inner catheter including a second lumen therein;
    wherein an outer surface of the stationary inner catheter is fixed to an inner surface of the catheter.

5. The device for crossing a lesion according to claim 4, further comprising:
    a mobile inner catheter disposed within the lumen of the catheter eccentric to the stationary inner catheter, the mobile inner catheter forming a third lumen therein, the mobile inner catheter configured to move axially and radially with respect to the stationary inner catheter.

6. The device for crossing a lesion according to claim 5, wherein a first proximal side of the loop is configured to be disposed within the second lumen, and wherein a second proximal side of the loop is configured to be disposed within the third lumen.

7. The device for crossing a lesion according to claim 1, wherein a first proximal side of the loop is configured to be disposed within the lumen of the catheter, and wherein a second proximal side of the loop is configured to be disposed outside of the lumen of the catheter.

8. The device for crossing a lesion according to claim 1, wherein a first proximal side of the loop and a second proximal side of the loop are configured to be disposed within the lumen of the catheter.

9. The device for crossing a lesion according to claim 1, wherein the crossing wire is twistable to form the loop having opposite sides that are intertwined.

10. The device for crossing a lesion according to claim 1, wherein the loop has a relaxed state such that opposite sides of the loop form an angle that is less than 90 degrees.

11. The device for crossing a lesion according to claim 1, wherein the loop has a relaxed state such that opposite sides of the loop form an angle that is less than 60 degrees.

12. The device for crossing a lesion according to claim 1, wherein the leading portion of the loop is rounded.

13. The device for crossing a lesion according to claim 1, wherein the leading portion of the loop is pointed.

14. The device for crossing a lesion according to claim 1, where the crossing wire is integrally formed.

15. The device for crossing a lesion according to claim 1, where the crossing wire has a single stiffness along its length.

16. The device for crossing a lesion according to claim 1, where the crossing wire has a variable stiffness along its length.

17. The device for crossing a lesion according to claim 1, wherein the crossing wire has a cross-section that is rectangular.

18. The device for crossing a lesion according to claim 1, wherein the proximal end of the crossing wire has a first stiffness, and wherein the leading portion of the loop has a second stiffness, wherein the first stiffness is greater than the second stiffness.

19. The device for crossing a lesion according to claim 1, wherein the loop includes a material that is radiopaque.

20. The device for crossing a lesion according to claim 1, wherein the crossing wire is configured to be rotatable back and forth through an angle less than 360 degrees while maintaining contact with the lesion to erode the lesion.

21. The device for crossing a lesion according to claim 1, wherein the crossing wire is configured to be twisted through an angle greater than 360 such that lateral opposing portions of the crossing wire become entwined beyond the distal end of the catheter.

* * * * *